United States Patent
Yamada et al.

(10) Patent No.: US 6,731,356 B2
(45) Date of Patent: May 4, 2004

(54) LIQUID CRYSTAL DISPLAY DEVICE AND METHOD FOR PRODUCING THE SAME

(75) Inventors: Nobuaki Yamada, Higashiosaka (JP); Fumikazu Shimoshikiryo, Tenri (JP); Yasuhiro Kume, Nara (JP); Shuichi Kozaki, Nara (JP); Takako Adachi, Tenri (JP); Shinichi Terashita, Nara (JP); Takashi Kurihara, Tenri (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 10/024,314

(22) Filed: Dec. 21, 2001

(65) Prior Publication Data

US 2002/0097362 A1 Jul. 25, 2002

Related U.S. Application Data

(62) Division of application No. 08/990,132, filed on Dec. 12, 1997, now Pat. No. 6,344,883.

(30) Foreign Application Priority Data

Dec. 20, 1996 (JP) .............................. 8-341590
Dec. 20, 1996 (JP) .............................. 8-341591
Aug. 29, 1997 (JP) .............................. 9-235137

(51) Int. Cl.[7] ..................... G02F 1/1333; G02F 1/1337; G02F 1/1339; C09K 19/02

(52) U.S. Cl. ................ 349/84; 349/130; 349/156; 349/178

(58) Field of Search ................ 349/84, 123, 130, 349/156, 178, 32

(56) References Cited

U.S. PATENT DOCUMENTS

| 4,896,149 A | | 1/1990 | Buzak et al. ............ 345/60 |
|---|---|---|---|
| 5,077,553 A | | 12/1991 | Buzak ........................ 345/87 |
| 5,184,236 A | * | 2/1993 | Miyashita et al. ........... 349/117 |
| 5,309,264 A | | 5/1994 | Lien et al. .................. 349/130 |
| 5,450,220 A | * | 9/1995 | Onishi et al. ................. 349/89 |
| 5,473,450 A | * | 12/1995 | Yamada et al. ............... 349/89 |
| 5,548,421 A | * | 8/1996 | Miyazaki ....................... 359/54 |
| 5,566,010 A | * | 10/1996 | Ishii et al. .................... 359/59 |
| 5,627,665 A | | 5/1997 | Yamada et al. ............. 349/156 |
| 5,666,179 A | | 9/1997 | Koma ........................ 349/130 |
| 5,748,275 A | * | 5/1998 | Sato et al. .................. 349/144 |
| 5,818,558 A | * | 10/1998 | Ogishima .................... 349/130 |
| 5,906,527 A | * | 5/1999 | Shaikh et al. ................. 445/24 |
| 6,014,188 A | * | 1/2000 | Yamada et al. ............... 349/32 |

FOREIGN PATENT DOCUMENTS

| CN | 1106929 A | 8/1995 |
|---|---|---|
| CN | 1127363 A | 7/1996 |
| EP | 0 634 685 A2 | 1/1995 |
| JP | 61-502128 | 9/1986 |

(List continued on next page.)

OTHER PUBLICATIONS

Buzak, "A new Active–Matrix Technique Using Plasma Addressing", SID 90 Digest, p. 420–423, 1990.*
"Liquid Crystal: Applications and Uses", D. Coates, pp 287–288, World Scientific, vol. 1, 1990.*
"Liquid Crystal: Applications and Uses", S. Kobayashi & A. Mochizuki, pp 254–258, World Scientific, vol. 3, 1992.*
Office Action of the People's Republic of China dated Mar. 29, 2002 (with English translation).

(List continued on next page.)

Primary Examiner—Dung Nguyen
(74) Attorney, Agent, or Firm—Nixon & Vanderhye, P.C.

(57) ABSTRACT

A liquid crystal display device of the present invention includes a pair of substrates and a liquid crystal layer provided between the substrates, wherein liquid crystal molecules in the liquid crystal layer have a negative dielectric anisotropy, and the liquid crystal molecules are aligned in a direction substantially vertical to the substrates when no voltage is being applied and are axis-symmetrically aligned in each of a plurality of pixel regions under application of a voltage.

20 Claims, 31 Drawing Sheets

FOREIGN PATENT DOCUMENTS

| | | |
|---|---|---|
| JP | 63-106624 | 5/1988 |
| JP | 1-217396 | 8/1989 |
| JP | 4-212928 | 8/1992 |
| JP | 4-265931 | 9/1992 |
| JP | 4-313788 | 11/1992 |
| JP | 4-338923 | 11/1992 |
| JP | 5-27242 | 2/1993 |
| JP | 06-118392 | 4/1994 |
| JP | 6-194655 | 7/1994 |
| JP | 06/301015 | 10/1994 |
| JP | 6-301036 | 10/1994 |
| JP | 6-308496 | 11/1994 |
| JP | 7-120728 | 5/1995 |
| JP | 7-199193 | 8/1995 |
| JP | 7-333612 | 12/1995 |
| JP | 8-95012 | 4/1996 |
| JP | 08-292423 | 11/1996 |
| JP | 10-133206 A | 5/1998 |
| WO | WO 85/04262 | 9/1985 |

OTHER PUBLICATIONS

Ong, Multi–Domain Homeotropic LCDs with Symmetrical Angular Optical Performance, 1992 SID International Symposium Digest of Papers, Boston, May 17–22, 1992, vol. 23, May 17, 1992, pp. 405–408.

Yamada et al., "Axially Symmetric Microcell (ASM) Mode: Electro–Optical Characteristics of New Display Mode with Excellent Wide Viewing Angle", 1995 SID International Symposium Digest of Technical Papers, Orlando, May 23–25, 1995, vol. 26, 1995, pp. 575–578.

\* cited by examiner (Observed from the front surface)

Axes are not shifted    Axes are shifted (Observed with a cell tilted)

(Areas of light and dark portions become nonuniform; as a result, roughness is observed)

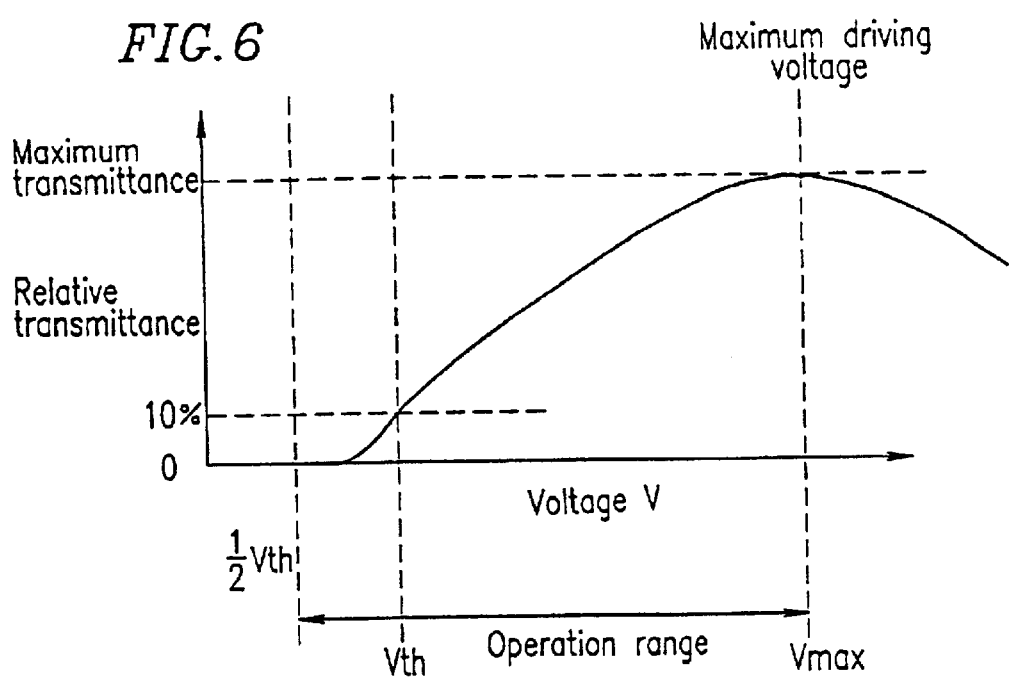

Directions of polarization axes of polarizing plates

Pixel region

Observed to be black

Extinction pattern

PRIOR ART

PRIOR ART

PRIOR ART

PRIOR ART

PRIOR ART

PRIOR ART (In the case of a large panel, a viewing angle is greatly changed depending upon the position of an observer)

*PRIOR ART*

LIQUID CRYSTAL DISPLAY DEVICE AND METHOD FOR PRODUCING THE SAME

This application is a Division of application Ser. No. 08/990,132 filed Dec. 12, 1997 now U.S. Pat. No. 6,344,833.

BACKGROUND OF THE INVENTION

1. Field of the Invention

The present invention relates to a liquid crystal display device and a method for producing the same. More specifically, the present invention relates to a liquid crystal display device having wide viewing angle characteristics and a method for producing the same.

2. Description of the Related Art

In the past, a liquid crystal display device (hereinafter, also referred to as an "LCD") in a twisted nematic (TN) mode has been known. The liquid crystal display device in a TN mode has poor viewing angle characteristics (i.e., a narrow viewing angle). As shown in FIG. 30A, when TN-LCD 200 is in a gray-scale display, liquid crystal molecules 202 are tilted in one direction. As a result, in the case where TN-LCD 200 is observed in viewing angle directions A and B as shown in FIG. 30A, apparent light transmittance varies depending upon the direction. Accordingly, the display quality (e.g., contrast ratio) of TN-LCD 200 greatly depends upon the viewing angle.

In order to improve the viewing angle characteristics of a liquid crystal display device by controlling the alignment state of liquid crystal molecules, it is required to align liquid crystal molecules in at least two directions in each pixel. Examples of such liquid crystal display devices includes those in an axially symmetric aligned microcell (ASM) mode in which liquid crystal molecules are axis-symmetrically aligned in each pixel. Referring to FIG. 30B, for example, when a liquid crystal display device 210 in an ASM mode in which a liquid crystal region 214 is surrounded by a polymer region 212 is in gray scales, liquid crystal molecules are aligned in two different directions. In the case where the liquid crystal display device 210 is observed in viewing angle directions represented by arrows A and B, apparent light transmittance is averaged. As a result, the light transmittance in the viewing angle directions A and B becomes substantially equal, whereby viewing angle characteristics are improved compared with those in a TN mode.

Examples of liquid crystal display devices in a mode having improved viewing angle characteristics (hereinafter, referred to as a "wide viewing angle mode") including an ASM mode will be described below.

(1) There is a technique for electrically controlling a transparent state or an opaque state by utilizing birefringence of a liquid crystal material in a liquid crystal display device which has polymer walls in a liquid crystal cell without polarizing plates and which does not require any alignment treatment. According to this technique, the ordinary index of liquid crystal molecules is matched with the refractive index of a supporting medium. Under the application of a voltage, the liquid crystal molecules are aligned, whereby a transparent state is displayed. When no voltage is being applied, the alignment of the liquid crystal molecules is disturbed, whereby a light scattering state is displayed.

For example, Japanese National Phase PCT Laid-open Publication No. 61-502128 discloses a technique for mixing liquid crystal with a photocurable or thermosetting resin, curing the resin to phase-separate liquid crystal from the resin, thereby forming liquid crystal droplets in the resin.

Furthermore, Japanese Laid-open Publication Nos. 4-338923 and 4-212928 disclose a liquid crystal display device in a wide viewing angle mode obtained by combining the device disclosed in Japanese National Phase PCT Laid-open Publication No. 61-502128 with polarizing plates in such a manner that polarization axes are orthogonal to each other.

(2) As a technique for improving viewing angle characteristics of a non-scattering type liquid crystal cell using polarizing plates, Japanese Laid-open Publication No. 5-27242 discloses a technique for producing a composite material containing liquid crystal and a polymer material from a mixture of liquid crystal and a photocurable resin by phase separation. According to this technique, the liquid crystal molecules in liquid crystal domains are randomly aligned by generated polymers, the liquid crystal molecules rise in different directions in each domain under the application of a voltage. Therefore, the apparent light transmittance observed in each direction becomes substantially equal (because retardation d·Δn is averaged, where d is a thickness of a liquid crystal layer and Δn is birefringence of a liquid crystal material), so that the viewing angle characteristics in gray scales are improved.

(3) Recently, in Japanese Laid-open Publication No. 7-120728, the inventors of the present invention have proposed a liquid crystal display device in which liquid crystal molecules are omnidirectionally aligned (e.g., in a spiral state) in pixel regions by controlling light using a photomask or the like during photopolymerization. This device uses a technique of axis-symmetrically aligning liquid crystal molecules by utilizing phase separation from a mixture of liquid crystal and a photocurable resin. The liquid crystal molecules are axis-symmetrically aligned when no voltage is being applied, and come closer to homeotropic alignment (alignment vertical to the substrates) under the application of a voltage, whereby the viewing angle characteristics are remarkably improved. This technique is a p-type display mode using a p-type liquid crystal material (i.e., a material with a positive dielectric anisotropy Δε).

As an example of a method for producing a device as described above, Japanese Laid-open Publication No. 8-95012 discloses a method for forming lattice-shaped polymer walls having a thickness smaller than the cell thickness in each pixel region, injecting a mixture of liquid crystal and a photocurable resin into the cell thus produced, and axis-symmetrically aligning liquid crystal molecules by utilizing two-phase regions in which a liquid crystal phase and a uniform phase exist. This production method does not use alignment films.

(4) Furthermore, Japanese Laid-open Publication No. 6-308496 discloses a liquid crystal display device in a wide viewing angle mode including an axis-symmetrical alignment film made of a crystalline polymer with a spherulite structure on the surface of a substrate.

(5) Japanese Laid-open Publication No. 6-194655 discloses a technique for coating an alignment film on a substrate and aligning liquid crystal molecules in a random direction without performing an alignment treatment such as rubbing.

There are techniques for dividing pixels into a plurality of regions and aligning liquid crystal molecules in each region in such a manner that the viewing angle characteristics in each region compensate for each other. Examples of the method will be described below.

(6) Japanese Laid-open Publication No. 63-106624 discloses a method for dividing each pixel into regions and performing an alignment treatment such as rubbing so that the rubbing directions in the respective regions become different.

FIGS. 31 and 32 show a liquid crystal display device obtained by the above method, having wide viewing angle characteristics and being capable of obtaining a display with a satisfactory contrast. FIG. 31 is a schematic plan view of the liquid crystal display device, and FIG. 32 is a cross-sectional view taken along the E–E' line in FIG. 31.

A pixel electrode (transparent electrode) 520 provided on each pixel, an alignment film 510, and a thin film transistor 513 driving the pixel electrode 520 are provided on one glass substrate 522 of the liquid crystal display device. A counter electrode (transparent electrode) 519 and an alignment film 509 are provided on the other glass substrate 521. The alignment films 509 and 510 are made of polyimide. A pixel B defined by the opposing transparent electrodes 519 and 520 is a square of 200 μm, for example, and a plurality of pixels B are arranged in a matrix. A band-shaped spacer 523 made of polyimide is provided in a center portion of the pixel electrodes 520, as a result of which each pixel B is divided into regions I and II by the band-shaped spacer 523.

The regions I and II are formed as schematically shown in FIG. 33. The glass substrates 521 and 522 are respectively subjected to a rubbing treatment in the arrow directions as shown in FIG. 33. In the past, in the case of providing the regions I with an alignment regulating force, the substrate 521 is subjected to a rubbing treatment with the regions II covered with a resist. Similarly, in the case of providing the regions II with an alignment regulating force, the substrate 521 is subjected to a rubbing treatment with the regions I covered with a resist.

According to the above technique, the alignment directions of liquid crystal molecules in the respective regions have the same spiral-type twist direction but form different angles with respect to the surface of the substrates. Due to the difference in angle with respect to the surface of the substrates, the liquid crystal molecules rise in different directions under the application of a voltage. Therefore, in the case where light is incident upon the substrate in a direction tilted from a direction normal to the substrate, the optical characteristics of the respective regions compensate for each other. As a result, the viewing angle dependence under the application of a voltage is cancelled in the regions having different orientations in each pixel between the substrates. Thus, optical characteristics with less viewing angle dependence are obtained. In particular, even when a viewing angle is varied in gray scales, there will be no phenomenon of gray-scale inversion.

(7) As a technique for making an alignment direction of an alignment film different, Japanese Laid-open Publication Nos. 7-199193 and 7-333612 disclose a technique for forming unevenness having a tilt in each pixel, thereby making the direction in which liquid crystal molecules are tilted different depending upon the region in each pixel. According to this technique, a pretilt angle is varied on a regional basis due to the different tilt directions in each pixel, thereby making the direction in which the liquid crystal molecules are tilted different. Thus, the viewing angle characteristics of a liquid crystal display device are improved. Japanese Laid-open Publication No. 7-199193 also discloses a homeotropic liquid crystal display device which uses an n-type ($\Delta\epsilon<0$) liquid crystal material and a homeotropic alignment film, and in which liquid crystal molecules are aligned in a direction vertical to substrates when no voltage is being applied and tilted in a direction horizontal to the substrates under the application of a voltage.

(8) Furthermore, Japanese Laid-open publication No. 6-301036 has proposed a liquid crystal display device having wide viewing angle characteristics and being capable of obtaining satisfactory display quality. FIG. 34 is a perspective view showing an external appearance of the liquid crystal display device, and FIG. 35 is a schematic cross-sectional view thereof. The liquid crystal display device includes a liquid crystal layer 612 having vertically aligned liquid crystal molecules 612A between a pair of electrode substrates. Pixel electrodes 611 are provided on one substrate 610, and counter electrodes 613 are provided on the other substrate (not shown). Each counter electrode 613 has openings 614 corresponding to central portions of each pixel.

The liquid crystal molecules 612A in a region of a liquid crystal layer corresponding to the opening 614 are stable, being vertically aligned under the application of a driving voltage. The liquid crystal molecules 612A on the periphery of the region corresponding to the opening 614 are also stable in alignment due to the interaction with the liquid crystal molecules 612A in the region corresponding to the opening 614. As a result, the liquid crystal molecules 612A in each pixel are aligned so as to face the central portion of the pixel corresponding to the opening 614. Thus, if the opening 614 of each pixel is provided at the identical position (e.g., a central portion of each pixel), the liquid crystal molecules are aligned similarly in each pixel. Because of this, even if a disclination line is similarly generated in each pixel, roughness of a display can be prevented. In FIG. 35, the reference numerals 615 and 616 denote gate bus lines, and 617 and 618 denote homeotropic alignment films.

Liquid crystal display devices (e.g., TFT-LCD) have been widely used as flat displays. However, large TFT-LCDs of a 20-inch or more diagonal screen, whose application for wall mounting has been expected, have not been commercially available. In recent years, as a candidate for realizing a large display device, a plasma address LCD (PALC) disclosed in Japanese Laid-open Publication No. 1-217396 has received attention.

FIG. 36 shows a cross-sectional structure of a PALC. A PALC 700 includes a liquid crystal layer 702 between a pair of substrates 701 and 711. A plurality of plasma chambers 713 are disposed between the substrate 711 and the liquid crystal layer 702. Each plasma chamber 713 is defined by the substrate 711, a dielectric sheet 716 opposing the substrate 711, and partition walls 712 provided between the substrate 711 and the dielectric sheet 716. Gas (e.g., helium, neon, etc.) sealed in the plasma chamber 713 is ionized by applying a voltage across an anode 714 and a cathode 715 formed on the surface of the substrate 711 in the plasma chamber 713, whereby plasma discharge occurs.

A plurality of plasma chambers 713 extend in the shape of stripes in a direction vertical to the drawing surface of FIG. 36 in such a manner as to be orthogonal to transparent electrodes 705 provided on the surface of the substrate 701 on the liquid crystal layer 702 side. Compared with a simple matrix type liquid crystal display device, the transparent electrodes 705 correspond to display electrodes (signal electrodes) and the plasma chambers 713 correspond to scanning electrodes. The substrate 711, the dielectric sheet 716, the plasma chambers 713, etc. are collectively called a plasma substrate 710.

Referring to FIG. 37, the basic principle of the PALC 700 will be described. The plasma chambers 713 are successively turned on, and the gas in the selected plasma chamber 713 is ionized. As shown in FIG. 37, under the condition that the plasma chamber 713 is ionized, a charge, in accordance with a voltage supplied from the signal lines to the transparent electrodes 705, is accumulated and held on a reverse surface of the dielectric sheet 716 on the plasma chamber 713 side. Thus, a signal voltage supplied from the signal lines is applied to a region of the liquid crystal layer 702 positioned above the ionized plasma chamber 713. When the plasma chamber 713 is not ionized, the charge is not supplied to the reverse surface of the dielectric sheet 716. Therefore, the signal voltage is not supplied to the region of the liquid crystal layer 702 positioned above the plasma chamber 713. Thus, the plasma chambers 713 function as scanning electrodes in a simple matrix type liquid crystal display device.

As a technique for producing a display with a large screen, Japanese Laid-open Publication No. 4-265931 discloses a technique of forming a plasma chamber structure on a glass substrate by a printing method using glass paste.

Japanese Laid-open Publication No. 4-313788 discloses a structure in which transparent electrodes are patterned in a direction of plasma chambers. In this structure, even when a thick dielectric sheet is interposed between plasma chambers and a liquid crystal layer for the purpose of enhancing the strength of the dielectric sheet, charge is prevented from dispersing on the liquid crystal layer side to cause bleeding of a display.

The above-described techniques have respective problems. Hereinafter, these problems will be described.

In the conventional liquid crystal display device in an ASM mode, a liquid crystal material with a positive dielectric anisotropy $\Delta\epsilon$ is used. In this display mode, as described above, liquid crystal molecules are axis-symmetrically aligned, so that outstanding display characteristics are obtained in an omnidirection. However, this liquid crystal display device has the following problems (1) to (4): (1) since this display mode is a normally white (NW) mode, a relatively high driving voltage is required for decreasing the light transmittance under the application of a voltage so as to obtain a high contrast; (2) in order to prevent light leakage when no voltage is being applied, it is required to prescribe an area of each light-blocking portion (e.g., a black matrix (BM)) to be large; (3) the liquid crystal display device in an ASM mode is difficult to produce, because a phase separation step requiring complicated temperature control is used for forming an ASM mode; and (4) since the liquid crystal display device in an ASM mode is difficult to produce, it is difficult to control the position of each central axis around which liquid crystal molecules are symmetrically aligned, the position of the central axis is varied depending upon the pixel, and the central axis is not positioned almost at the center of the pixel region; as a result, when the liquid crystal display device is observed in an oblique direction, a rough display with unsatisfactory quality is obtained.

Furthermore, in the liquid crystal display devices using a liquid crystal material with a positive dielectric anisotropy $\Delta\epsilon$ as described in the above-mentioned (6) and (7), alignment directions of the liquid crystal molecules on the division lines become discontinuous under the application of a voltage, i.e., disclination lines are generated, causing the decrease in contrast ratio. Furthermore, in this liquid crystal display device, in order to produce a plurality of divided regions, a resist is coated onto an alignment film, followed by rubbing on a region basis. According to this method, the alignment film is exposed to a resist material, a developing solution, a release agent, etc. Therefore, ions contained in the resist, the developing solution, the release agent, etc., remain on the alignment film after the resist is peeled off. The remaining ions may have an adverse effect on the display characteristics by moving during the operation of the liquid crystal display device to deteriorate the charge-holding characteristics of the liquid crystal material and to cause a phenomenon such as an image burn-in. Furthermore, depending upon the kinds of the alignment film and the resist to be combined, the alignment film is damaged to lose an alignment regulating force. Thus, such a liquid crystal display device is low both in production efficiency and production stability.

Furthermore, in the liquid crystal display device described in the above (8), the liquid crystal molecules are axis-symmetrically aligned only in the opening of the counter electrode. More specifically, the liquid crystal molecules on the periphery of the pixel away from the opening are not axis-symmetrically aligned. Thus, the liquid crystal molecules are randomly aligned, which may cause a rough display. Furthermore, the positions or sizes of liquid crystal domains (regions where the alignment direction of the liquid crystal molecules are continuous, and disclination lines are not generated) are not defined, so that disclination lines cannot be prevented from being generated in pixels, particularly, causing a rough display in gray scales.

The PALC has the following problems. The PALC mainly uses a TN mode. When a TN mode in which display quality depends upon a viewing angle is applied to a display device with a large screen, even when an observer's position is fixed, the viewing angle (a and b) is varied depending upon the position of a display screen to be observed, as shown in FIG. 38. Therefore, the display quality becomes unsatisfactory in the display screen.

In the case of the PALC in a TN mode, considering the viewing angle dependence of the TN mode, polarization axes of polarizing plates are set at 45° from a crosswise direction on the display surface, thereby adjusting the sideward viewing angle characteristics seen by an observer in a satisfactory direction. In this case, at a portion such as an attachment surface between the plasma substrate and the thin glass sheet where the difference in refractive index is present, an attachment portion becomes visible due to the birefringence and the difference in refractive index of polarized light on the attachment surface, whereby light leakage, which is critical to a display, occurs in a crosswise direction.

The PALC uses a display mode using p-type liquid crystal material, such as a NW mode and a TN mode. In the PALCs in these display modes, a sufficient contrast ratio cannot be obtained. This is caused by the nonuniform voltage (electric field) applied to the liquid crystal layer due to the nonuniform plasma charge. In the NW mode using p-type liquid crystal ($\Delta\epsilon>0$), particularly, a black level under the application of a voltage is decreased, resulting in a great decrease in contrast ratio.

SUMMARY OF THE INVENTION

A liquid crystal display device of the present invention includes a pair of substrates and a liquid crystal layer provided between the substrates, wherein liquid crystal molecules in the liquid crystal layer have a negative dielectric anisotropy, and the liquid crystal molecules are aligned in a direction substantially vertical to the substrates when no voltage is being applied and axis-symmetrically aligned in each of a plurality of pixel regions under application of a voltage.

In one embodiment of the present invention, a thickness ($d_{in}$) of the liquid crystal layer in the pixel region is larger than a thickness ($d_{out}$) of the liquid crystal layer outside of the pixel region, and the device includes a homeotropic alignment layer in a region corresponding to the pixel region on a surface of at least one of the substrates on the liquid crystal layer side.

In another embodiment of the present invention, at least one of the substrates has convex portions defining the pixel region on a surf ace on the liquid crystal layer side.

In another embodiment of the present invention, the thickness of the liquid crystal layer in the pixel region is largest at a central portion of the pixel region and continuously decreases toward a peripheral portion of the pixel region.

In another embodiment of the present invention, the thickness of the liquid crystal layer in the pixel region is axis-symmetrically changed around the central portion of the pixel region.

In another embodiment of the present invention, the above-mentioned liquid crystal display device further includes a projection at the central portion of the pixel region, wherein the liquid crystal molecules are axis-symmetrically aligned around the projection under the application of a voltage.

In another embodiment of the present invention, a retardation d·Δn of the liquid crystal layer is in a range of about 300 nm to about 500 nm.

In another embodiment of the present invention, a twist angle of the liquid crystal layer is in a range of about 45° to about 110°.

In another embodiment of the present invention, the above-mentioned liquid crystal display device includes a pair of polarizing plates disposed in crossed Nicols on both sides of the liquid crystal layer, and a phase difference plate having a relationship, in which a refractive index $n_{x,y}$ in an in-plane direction is greater than a refractive index $n_z$ in a direction vertical to a plane, is provided on at least one of the polarizing plates.

In another embodiment of the present invention, an axis-symmetrical alignment fixing layer which provides the liquid crystal molecules with an axis-symmetrical pretilt angle is further formed on a surface of at least one of the substrates on the liquid crystal layer side.

In another embodiment of the present invention, the axis-symmetrical alignment fixing layer contains a photo-curable resin.

A method for producing a liquid crystal display device of the present invention includes the steps of: forming a homeotropic alignment layer on a pair of substrates, respectively; disposing a mixture containing a liquid crystal material having a negative dielectric anisotropy and a photocurable resin between the homeotropic alignment layers on the substrates; and curing the photocurable resin while applying a voltage higher than a threshold voltage of the liquid crystal material to the mixture, so as to form an axis-symmetrical alignment fixing layer providing the liquid crystal molecules with an axis-symmetrical pretilt angle.

In one embodiment of the present invention, the above-mentioned method further includes the step of forming convex portions defining pixel regions on a surface of at least one of the substrates before the step of forming the homeotropic alignment layers on the substrates.

A liquid crystal display device of the present invention includes: a plasma substrate having plasma chambers for performing plasma discharge; a counter substrate having signal electrodes; and a liquid crystal layer provided between the plasma substrate and the counter substrate, the device being driven by the signal electrodes and the plasma chambers, wherein liquid crystal molecules in the liquid crystal layer have a negative dielectric anisotropy, and the liquid crystal molecules are aligned in a direction substantially vertical to the substrates when no voltage is being applied and axis-symmetrically aligned in each of a plurality of pixel regions under application of a voltage.

In one embodiment of the present invention, a thickness ($d_{in}$) of the liquid crystal layer in the pixel region is larger than a thickness ($d_{out}$) of the liquid crystal layer outside of the pixel region, and the device includes a homeotropic alignment layer in a region corresponding to the pixel region on a surface of at least one of the substrates on the liquid crystal layer side.

In another embodiment of the present invention, at least one of the counter substrate and the plasma substrate has convex portions defining the pixel region on a surface on the liquid crystal layer side.

In another embodiment of the present invention, the thickness of the liquid crystal layer in the pixel region is largest at a central portion of the pixel region and continuously decreases toward a peripheral portion of the pixel region.

In another embodiment of the present invention, the thickness of the liquid crystal layer in the pixel region is axis-symmetrically changed around the central portion of the pixel region.

In another embodiment of the present invention, the above-mentioned liquid crystal display device includes a pair of polarizing plates disposed in crossed-Nicols on both sides of the liquid crystal layer, a polarization axis of one of the polarizing plates being parallel to an extending direction of the signal electrodes or the plasma chambers.

In another embodiment of the present invention, an axis-symmetrical alignment fixing layer which provides the liquid crystal molecules with an axis-symmetrical pretilt angle is further formed on a surface of at least one of the plasma substrate and the counter substrate on the liquid crystal layer side.

In another embodiment of the present invention, the axis-symmetrical alignment fixing layer contains a photo-curable resin.

A liquid crystal display device of the present invention includes: a pair of substrates and a liquid crystal layer provided between the substrates, wherein liquid crystal molecules in the liquid crystal layer have a negative dielectric anisotropy, and the liquid crystal molecules are aligned in a direction substantially vertical to the substrates when no driving voltage is being applied and axis-symmetrically aligned around an axis-symmetrical alignment central axis in each of a plurality of pixel regions under application of a driving voltage, and convex portions defining the pixel region are provided on a surface of at least one of the substrates on the liquid crystal layer side, and a treatment for controlling a position of the axis-symmetrical alignment central axis is conducted.

In one embodiment of the present invention, the above-mentioned liquid crystal display device includes a region in which the liquid crystal molecules keep a homeotropic alignment state under application of an axis-symmetrical alignment central axis forming voltage at each predetermined position in the plurality of pixel regions.

In another embodiment of the present invention, Sa is an area of the region in which the liquid crystal molecules keep a homeotropic alignment state under the application of the axis-symmetrical alignment central axis forming voltage, A is an area of the pixel region, and Sa/A satisfies the relationship 0<Sa/A<4%.

In another embodiment of the present invention, the above-mentioned liquid crystal display device includes an axis-symmetrical alignment central axis forming portion at a predetermined position in each of the plurality of pixel regions, and the axis-symmetrical alignment central axis of the liquid crystal molecules is formed corresponding to the axis-symmetrical alignment central axis forming portion.

In another embodiment of the present invention, Sb is an area of the axis-symmetrical alignment central axis forming portion, A is an area of the pixel region, and Sb/A satisfies the relationship 0<Sb/A<4%.

In another embodiment of the present invention, a thickness of the liquid crystal layer in the pixel region is larger than a thickness of the liquid crystal layer outside of the pixel region.

In another embodiment of the present invention, the thickness of the liquid crystal layer in the pixel region is largest at a central portion of the pixel region and continuously decreases from the central portion to a peripheral portion of the pixel region.

In another embodiment of the present invention, the thickness of the liquid crystal layer in the pixel region is axis-symmetrically changed around the central portion of the pixel region.

In another embodiment of the present invention, an axis-symmetrical alignment fixing layer is provided on a surface of at least one of the substrates on the liquid crystal layer side.

In another embodiment of the present invention, the axis-symmetrical alignment fixing layer contains a photo-curable resin.

A method for producing a liquid crystal display device is provided. The device includes a pair of substrates and a liquid crystal layer provided between the substrates, liquid crystal molecules in the liquid crystal layer having a negative dielectric anisotropy, the liquid crystal molecules being aligned in a direction substantially vertical to the substrates when no driving voltage is being applied and being axis-symmetrically aligned around an axis-symmetrical alignment central axis in each of a plurality of pixel regions under application of a driving voltage. The method includes the step of performing an axis-symmetrical alignment central axis forming process.

In one embodiment of the present invention, the axis-symmetrical alignment central axis forming process includes the steps of: disposing a precursor mixture containing a liquid crystal material and a photocurable material between the substrates; and curing the photocurable material while applying an axis-symmetrical alignment central axis forming voltage to the precursor mixture.

In another embodiment of the present invention, the axis-symmetrical alignment central axis forming voltage is ½ or more of a threshold voltage of the liquid crystal material.

In another embodiment of the present invention, the axis-symmetrical alignment central axis forming voltage is an AC voltage.

In another embodiment of the present invention, a frequency of the AC voltage is 1 Hz or more.

Thus, the invention described herein makes possible the advantages of (1) providing a liquid crystal display device including a liquid crystal region in which liquid crystal molecules are axis-symmetrically aligned in each pixel region, having outstanding viewing angle characteristics in an omnidirection and a high contrast without roughness; (2) providing a plasma address LCD having outstanding viewing angle characteristics and a high contrast; and (3) providing a method for producing the liquid crystal display devices as described above with ease.

These and other advantages of the present invention will become apparent to those skilled in the art upon reading and understanding the following detailed description with reference to the accompanying figures.

BRIEF DESCRIPTION OF THE DRAWINGS

FIG. 6 is a graph showing a voltage-transmittance curve of a liquid crystal display device including a liquid crystal layer with $d \cdot \Delta n = 450$ nm.

DESCRIPTION OF THE PREFERRED EMBODIMENTS

Hereinafter, preferred embodiments of the present invention will be described with reference to the drawings. It should be noted that the present invention is not limited thereto.

Embodiment 1

Basic Operation

Figure 1A:
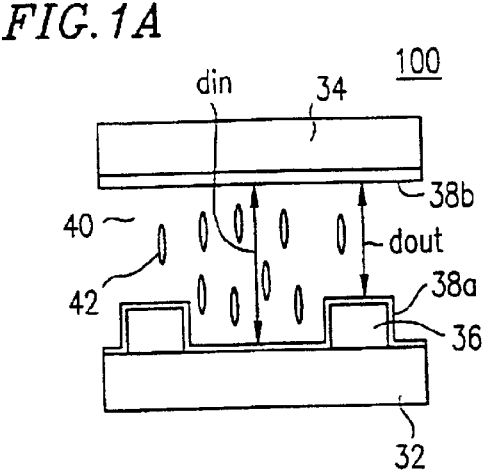
FIGS. 1A through 1D are schematic views illustrating the operation principle of a liquid crystal display device in an embodiment of the present invention.
Figure 1C:
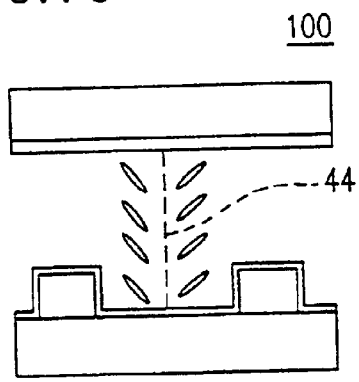
Figure 1B:
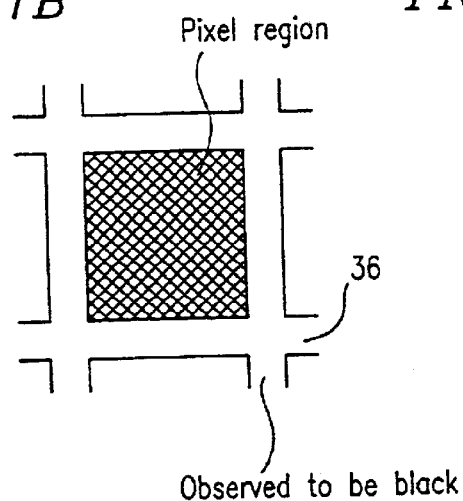
Figure 1D:
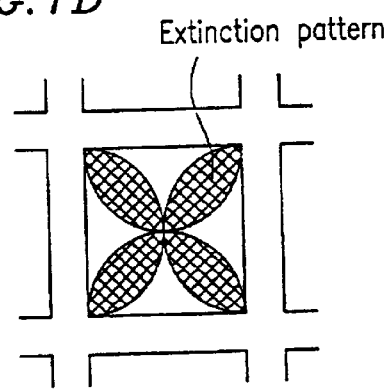

Referring to FIGS. 1A through 1D, the operation principle of a liquid crystal display device 100 in an embodiment of the present invention will be described. FIG. 1A is a schematic cross-sectional view of the liquid crystal display device 100 when no voltage is being applied, and FIG. 1C is a schematic cross-sectional view thereof under the application of a voltage. FIG. 1B shows results obtained by observing the upper surface of the liquid crystal display device 100 when no voltage is being applied with a polarizing microscope in crossed-Nicols, and FIG. 1D shows results obtained by observing the upper surface of the liquid crystal display device 100 under the application of a voltage with a polarizing microscope in crossed-Nicols.

The liquid crystal display device 100 includes a liquid crystal layer 40 containing an n-type liquid crystal material (liquid crystal molecules) 42 with a negative dielectric anisotropy $\Delta\epsilon$ between a pair of substrates 32 and 34. Homeotropic alignment layers 38a and 38b are provided on the surfaces of the substrates 32 and 34 in contact with the liquid crystal layer 40. Convex portions 36 are formed on the surface of at least one of the substrates 32 and 34 on the liquid crystal layer 40 side. Because of the convex portions 36, the liquid crystal layer 40 has two different thicknesses $d_{out}$ and $d_{in}$. Consequently, a liquid crystal region exhibiting axis-symmetrical alignment under the application of a voltage is defined as a region surrounded by the convex portions 36, as described later. In FIGS. 1A through 1D, electrodes for applying a voltage to the liquid crystal layer 40 formed on the substrates 32 and 34 are omitted.

As shown in FIG. 1A, the liquid crystal molecules 42 are aligned by an alignment regulating force of the homeotropic alignment layers 38a and 38b in a direction vertical to the substrates 32 and 34 when no voltage is being applied. When pixel regions are observed when no voltage is being applied with a polarizing microscope in crossed-Nicols, a black field of view (normally black mode) is exhibited as shown in FIG. 1B. Upon the application of a voltage, the liquid crystal molecules 42 having a negative dielectric anisotropy $\Delta\epsilon$ are provided with a force which aligns the major axes of the liquid crystal molecules 42 in a direction vertical to the electric field direction. Therefore, the liquid crystal molecules 42 are tilted from a direction vertical to the substrates 32 and 34 (gray-scale display state), as shown in FIG. 1C. When the pixel regions in this state are observed with a polarizing microscope in crossed-Nicols, extinction patterns are observed in the directions of polarization axes as shown in FIG. 1D.

Figure 2:
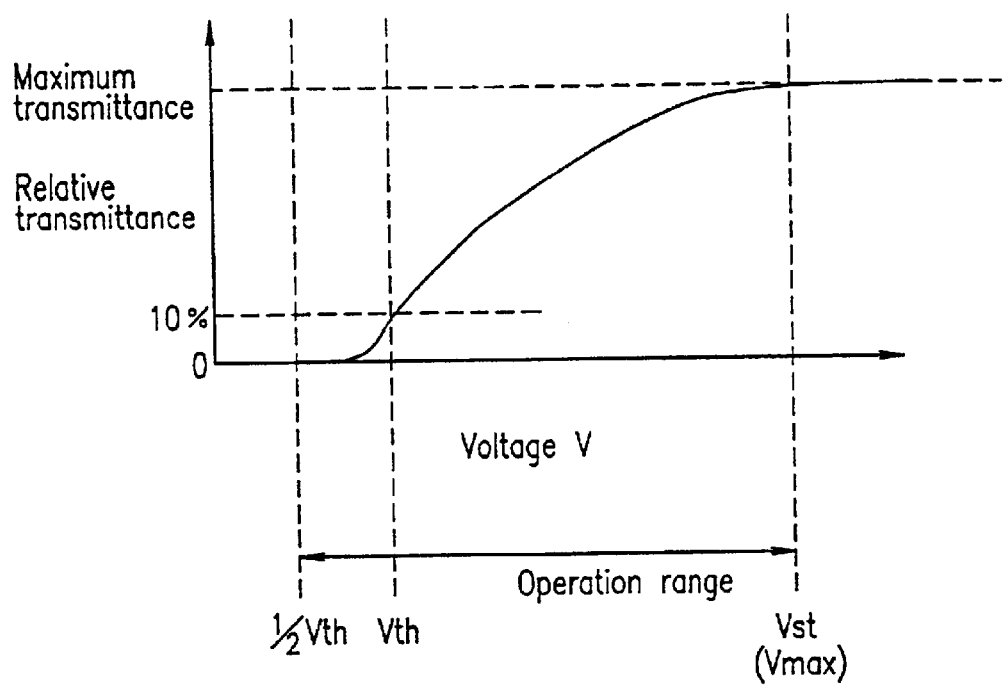
FIG. 2 is a graph showing a voltage-transmittance curve of the liquid crystal display device shown in FIGS. 1A through 1D.

FIG. 2 shows a voltage-transmittance curve of the liquid crystal display device 100 of the present invention. The abscissa axis represents a voltage applied to the liquid crystal layer 40, and the ordinate axis represents a relative transmittance. When a voltage is increased from a normally black state when no voltage is being applied, the transmittance gradually increases. A voltage at which the relative transmittance with respect to a saturated transmittance becomes 10% is referred to as $V_{th}$ (threshold voltage). When the voltage is further increased, the transmittance further increases to reach saturation. A voltage at which the transmittance is saturated is referred to as $V_{st}$ (saturation voltage). In the case where a voltage applied to the liquid crystal layer 40 is between $½ V_{th}$ and $V_{st}$, the transmittance reversibly changes in the operation range shown in FIG. 2. Under the application of a voltage in the vicinity of $½ V_{th}$, the liquid crystal molecules are aligned in a direction almost vertical to the substrates, while remembering the symmetry with respect to central axes in axis-symmetrical alignment. Thus, when a voltage exceeding $½ V_{th}$ is applied, it is considered that the liquid crystal molecules reversibly return to the "remembered" axis-symmetrical alignment state. However, when a voltage to be applied becomes lower than $½ V_{th}$, the liquid crystal molecules are aligned in a direction almost vertical to the substrates without remembering the symmetry with respect to the central axes in the axis-symmetrical alignment. Thus, even when a voltage exceeding $½ V_{th}$ is applied again, the direction in which the liquid crystal molecules are tilted is not uniquely determined. Therefore, due to the presence of a plurality of central axes in axis-symmetrical alignment, the transmittance does not become stable. More specifically, a plurality of central axes are once formed in the regions defined by the convex portions 36 (i.e., pixel regions). For example, at a stage where an n-type liquid crystal material is injected into a liquid crystal cell, the liquid crystal molecules behave in the same way as in the case of an applied voltage of less than $½ V_{th}$.

Thus, the display mode in the present embodiment becomes practically useful by applying a voltage realizing axis-symmetrical alignment in the initial display, and using the device in the range of a voltage at which the alignment is stable after the commencement of the display.

Convex Portions Defining Pixel Regions

As shown in FIG. 1A, the liquid crystal display device 100 of the present invention has convex portions 36 so as to surround the pixel regions. In the case where the thickness (cell gap) of the liquid crystal layer 40 is uniform without convex portions 36, the positions and sizes of liquid crystal domains (continuously aligned regions: regions with no disclination lines) are not defined. Therefore, the liquid crystal molecules are aligned in a random direction, resulting in a rough display in gray scales.

According to the present invention, the convex portions 36 define the positions and sizes of the liquid crystal regions exhibiting axis-symmetrical alignment. The convex portions 36 are formed for the purpose of controlling the thickness of the liquid crystal layer 40 and weakening the interaction of the liquid crystal molecules between the pixel regions. Regarding the thickness of the liquid crystal layer 40, it is preferable that the thickness $d_{out}$ of the liquid crystal layer 40 on the periphery of the pixel region is smaller than the thickness $d_{in}$ of the liquid crystal layer 40 in the pixel region (opening portion), i.e., $d_{in} > d_{out}$, and the relationship $0.2 \times d_{in} \leq d_{out} \leq 0.8 \times d_{in}$ is satisfied. More specifically, in the case of $0.2 \times d_{in} > d_{out}$, the effect of weakening the interaction of the liquid crystal molecules between the pixel regions by the convex portions 36 is not sufficient, and it may be difficult to form a single axis-symmetrically aligned region in each pixel region. Furthermore, in the case of $d_{out} > 0.8 \times d_{in}$, it may be difficult to inject a liquid crystal material into a liquid crystal cell.

It is noted that a "pixel" is generally defined as the minimum unit for performing a display. The term "pixel region" used herein refers to a partial region of a display device corresponding to the "pixel". In the case of pixels having a large aspect ratio (i.e., long pixels), a plurality of pixel regions may be formed with respect to one long pixel. The number of pixel regions formed corresponding to pixels is preferably as small as possible, as long as the axis-symmetrical alignment is stably formed. The term "axis-symmetrical alignment" refers to, for example, radial alignment, tangential alignment, etc.

Control of Positions of Central Axes in Axis-Symmetrical Alignment

Figure 3A:
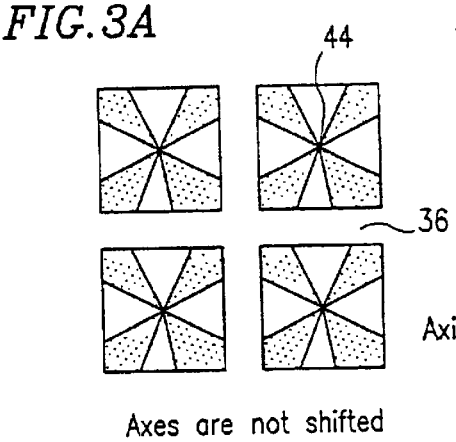
FIGS. 3A through 3D are schematic views illustrating the relationship between the position of a central axis of an axis-symmetrically aligned region and the display quality.
Figure 3B:
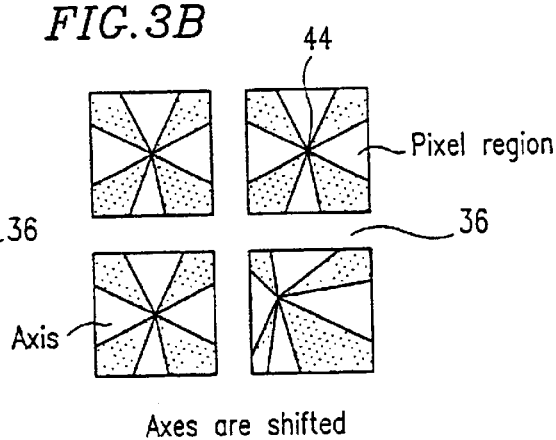
Figure 3C:
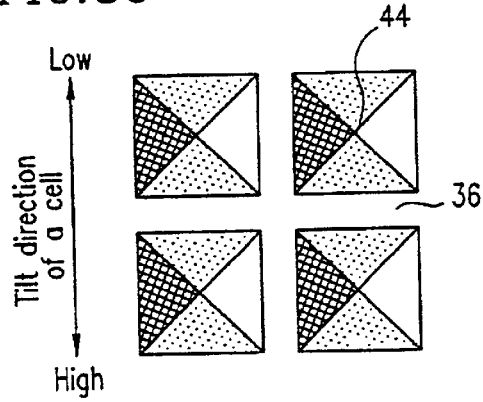
Figure 3D:
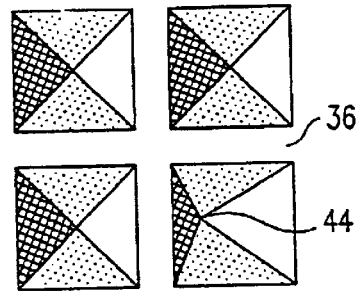

The positions of central axes in the axis-symmetrically aligned regions generated under the application of a voltage have a great effect on display quality. Referring to FIGS. 3A through 3D, the relationship between the positions of central axes and the display quality will be described. As shown in FIG. 3A, in the case where a central axis 44 is positioned at the center of each pixel region, even when a display surface is observed with a cell tilted, all the pixel regions are observed in the same way as shown in FIG. 3C. As shown in FIG. 3B, in the case where the central axes 44 are positioned shifted away from the centers of the pixel regions, the pixel regions with the shifted central axes are observed in a different way from the other pixel regions as shown in FIG. 3D, which results in a rough display. This problem becomes particularly remarkable in gray scales.

Figure 4A:
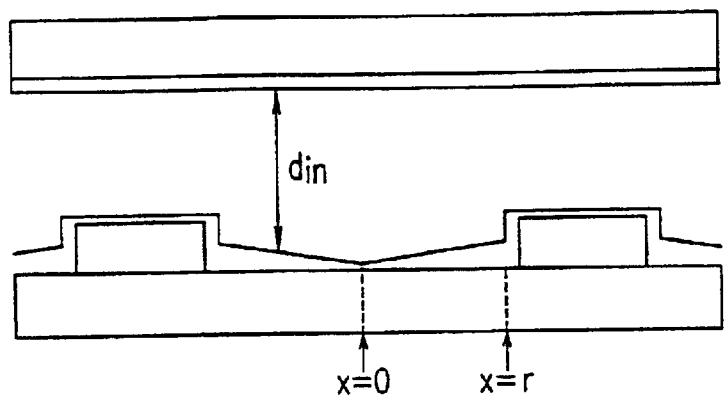
FIGS. 4A and 4B are schematic views illustrating a thickness $d_{in}(x)$ of a liquid crystal layer of the liquid crystal display device in a embodiment of the present invention.
Figure 4B:
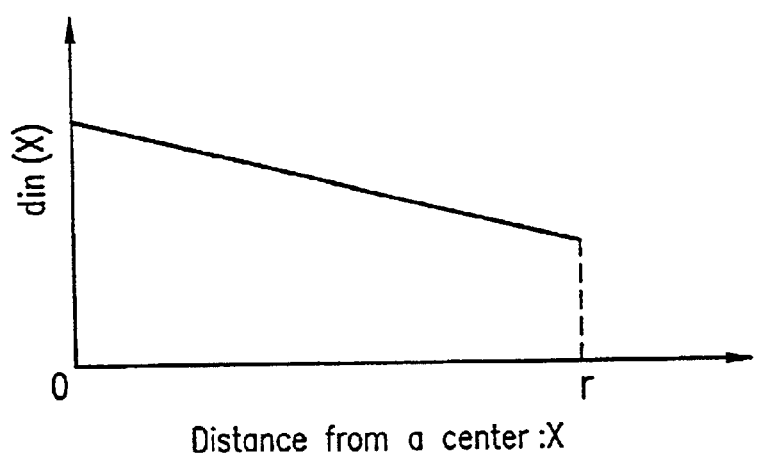

The positions of central axes in axis-symmetrical alignment can be controlled by adjusting the thickness $d_{in}(x)$ of the liquid crystal layer in the pixel regions. As shown in FIGS. 4A and 4B, the thickness $d_{in}(x)$ of the liquid crystal layer is continuously changed so that the thickness $d_{in}(x=0)$ of the liquid crystal layer becomes maximum and the thickness $d_{in}(x=r)$ becomes minimum, where $x=0$ at the center of the pixel region, and $x=r$ at one end of the pixel region. It is preferable that the differential coefficient of $d_{in}(x)$ is always negative and continuous from $x=0$ to $x=r$. In view of the symmetry of the viewing angle characteristics, it is preferable that the thickness of the liquid crystal layer is as symmetric as possible with respect to the center of each pixel region.

Figure 5A:
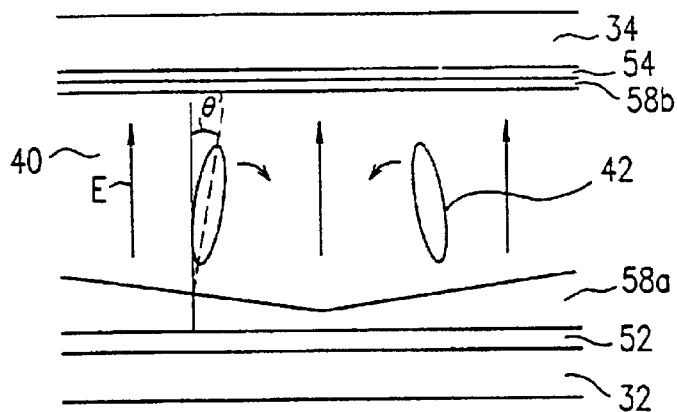
FIGS. 5A through 5C are schematic cross-sectional views illustrating a pixel region in the liquid crystal display device in the embodiment of the present invention.
Figure 5B:
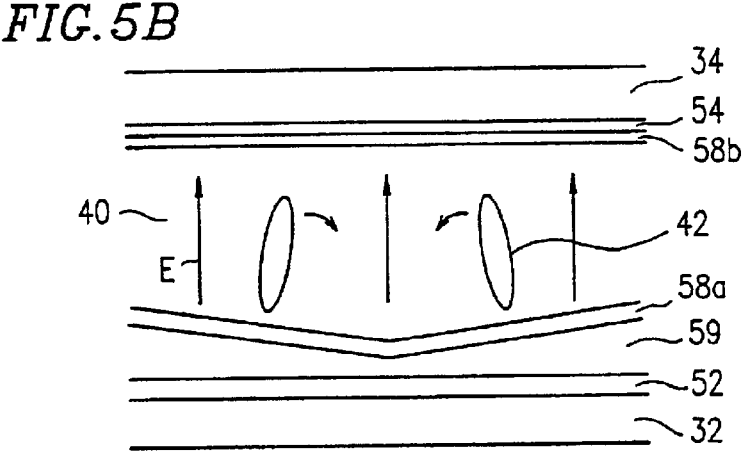
Figure 5C:
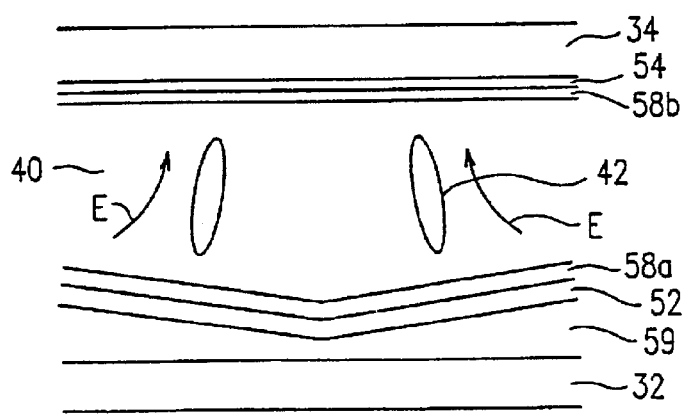

The axis-symmetrical alignment is formed with good reproducibility by controlling the thickness of the liquid crystal layer as described above. This mechanism will be described with reference to FIGS. 5A through 5C. FIGS. 5A through 5C are schematic cross-sectional views illustrating a pixel region of the liquid crystal display device of the present invention.

As shown in FIG. 5A, a display electrode 52 is formed in a pixel region on the surface of one substrate 32, and a homeotropic alignment layer 58a is formed so as to cover the display electrode 52. The homeotropic alignment layer 58a has a cross-section in which the thickness $d_{in}$ of the liquid crystal layer 40 changes as shown in FIGS. 4A and 4B. The changes in the thickness $d_f$ of the homeotropic alignment layer 58a with respect to a position x is opposite to the changes in the thickness of the liquid crystal layer 40. Therefore, it is preferable that the differential coefficient of $d_f(x)$ of the homeotropic alignment layer 58a is positive. A counter electrode 54 is formed on the surface of the other substrate 34 on the liquid crystal layer 40 side, and a homeotropic alignment layer 58b is formed so as to cover the counter electrode 54. The homeotropic alignment layer 58b has a flat cross-section.

Liquid crystal molecules 42 in the vicinity of the homeotropic alignment layer 58a are aligned in a direction vertical to the surface of the homeotropic alignment layer 58a, so that they are tilted from the substrate surface. Thus, when a voltage is applied across the electrodes 52 and 54, the major axes of the liquid crystal molecules 42 become tilted from an electrical field direction E. As a result, the liquid crystal molecules 42 are tilted by the electrical field E only in directions represented by arrows in FIG. 5A. A tilt angle θ' of the liquid crystal molecule from a direction normal to the substrate surface preferably satisfies the relationship 0<θ'≦3°. When θ' exceeds about 3°, there is a large possibility that a phase difference may be caused by the liquid crystal molecules and light may leak to decrease the contrast ratio.

As described above, the cross-sectional shape (thickness) of the homeotropic alignment layer is changed to vary the thickness of the liquid crystal layer 40 as described with reference to FIGS. 4A and 4B, whereby the positions of central axes in axis-symmetrical alignment can be controlled, and the ax-s-symmetrical alignment can be realized with good reproducibility.

In the example shown in FIG. 5A, although the thickness of the liquid crystal layer 40 is controlled by the cross-sectional shape of the homeotropic alignment layer 58a, the method for controlling the thickness of the liquid crystal display device 40 is not limited thereto. For example, as shown in FIG. 5B, a solid dielectric layer 59 having a desired cross-section may be separately formed, and the homeotropic alignment layer 58a having a uniform thickness may be formed thereon. The solid dielectric layer 59 can be formed by using a conventionally used overcoat agent, more specifically, an epoxy-type coating agent, an epoxyacrylate-type coating agent, and the like. In the present embodiment, the thickness of the thickest portion of the solid dielectric layer 59 is, for example, in the range of 500 to 10000 nm, and the thickness of the thinnest portion is, for example, in the range of 0 to 5000 nm.

In the case where the thickness of the liquid crystal layer 40 is controlled by using the solid dielectric layer 59, the solid dielectric layer 59 is preferably formed on the display electrode 52. As shown in FIG. 5C, when the display electrode 52 is formed on the solid dielectric layer 59, the electric field direction E is tilted from the substrate surface, so that in most cases, the direction in which the liquid crystal molecules are tilted is not uniquely determined.

Liquid Crystal Material

The liquid crystal material used in the present invention is of an n-type which has a negative dielectric anisotropy (Δε<0). The absolute value of Δε can be appropriately determined depending upon the purpose. In general, considering that a driving voltage is decreased, the absolute value is preferably large.

Retardation d·Δn under the application of a voltage is an important factor which influences critical device characteristics such as transmittance and viewing angle characteristics of a device. In the display mode of the present invention, the retardation peculiar to a liquid crystal cell determined by the product of Δn peculiar to a liquid crystal material and a thickness d of a liquid crystal layer is not necessarily defined to be an optimum value. According to the present invention, the retardation at the maximum driving voltage to be used is important, which will be described below.

FIG. 6 shows a voltage-transmittance curve of a liquid crystal display device having a retardation value larger than the optimum retardation value (first minimum condition under which a transmittance becomes maximum: d·Δn=450 nm). In such a liquid crystal display device, it is not required to use a voltage at which a transmittance exceeds the maximum point of a relative transmittance, and the device may be driven in a region where the relative transmittance monotonously increases. More specifically, a voltage at which the relative transmittance becomes maximum may be set as the maximum driving voltage $V_{max}$ in FIG. 6.

Regarding the range of retardation, a product d·Δn (retardation) of apparent Δn (anisotropy of a refractive index: a value at the maximum driving voltage) of liquid crystal molecules when a liquid crystal cell is produced and an average thickness d of the liquid crystal layer is preferably in the range of about 300 nm to about 500 nm. There is a second minimum condition (retardation: about 1000 nm to about 1400 nm) for the transmittance to become local maximum. However, the second minimum condition is not preferable since the viewing angle characteristics when no voltage is being applied decrease. Furthermore, the relationship between the level of an applied voltage and the transmittance becomes inverted depending upon the viewing angle, what is called, a gray-scale inversion (contrast inversion) phenomenon occurs under the second minimum condition, which is not preferable.

The twist angle of the liquid crystal molecules in the liquid crystal layer is also an important factor determining the transmittance of the liquid crystal display device. According to the present invention, the twist angle at the maximum driving voltage is as important as the retardation. In principle, the transmittance of the liquid crystal display device becomes maximum in the case where the twist angle is 90° and 270°. However, in the case of the twist angle of 270°, it is difficult to stably produce axis-symmetrical alignment, so that the twist angle in the vicinity of 90° at which the transmittance becomes maximum in the voltage-transmittance curve is preferable. The twist angle under the application of the maximum driving voltage is preferably in the range of about 45° to about 110°. According to the present invention, since the n-type liquid crystal molecules are used, the apparent twist angle of the liquid crystal molecules depends upon a voltage. The twist angle when no voltage is being applied is almost 0°, and the twist angle increases with the increase in the applied voltage. When a sufficient voltage is applied, the twist angle approaches that peculiar to the liquid crystal material.

The combination of the twist angle and the retardation in the above-mentioned range under the application of the maximum driving voltage is more preferable, because it allows the transmittance to approach the maximum value more effectively.

Photocurable Resin

As described above with reference FIG. 2, it is preferable that a voltage of ½ $V_{th}$ or more is always applied to the liquid crystal display device of the present invention. If a voltage is applied to liquid crystal molecules aligned in a direction vertical to the substrates, the direction in which the liquid crystal molecules are tilted is not uniquely determined. As a result, a plurality of central axes are transiently formed. If a voltage is continued to be applied, a single central axis is formed in each region defined by the convex portions, and this state is stably maintained as long as a voltage of ½ $V_{th}$ or more is applied.

An axis-symmetrical alignment fixing layer is formed by curing a photocurable resin mixed in a liquid crystal material under the application of a voltage of ½ $V_{th}$ or more for stabilizing axis-symmetrical alignment. The axis-symmetrical alignment fixing layer is capable of stabilizing the axis-symmetrical alignment. After the photocurable resin is cured, a plurality of central axes are not formed even when a voltage of ½ $V_{th}$ or more is removed. Thus, the axis-symmetrical alignment is formed with good reproducibility. The axis-symmetrical fixing layer will be described in detail later.

As the photocurable resin used in the present invention, an acrylate type resin, a methacrylate type resin, a styrene type resin, and derivatives thereof can be used. By adding a photopolymerization initiator to these resins, the photocurable resin can be cured more efficiently. A thermosetting resin can also be used.

The adding amount of the curable resin (photocurable or thermosetting resin) is not particularly limited in the present invention, with the optimum amount being variable depending upon the material. However, it is preferable that the content of the resin (% based on the total weight including the weight of the liquid crystal material) is about 0.1% to about 5%. When the content is less than about 0.1%, the axis-symmetrical alignment state cannot be stabilized by the cured resin. When the content exceeds about 5%, the effect of the homeotropic alignment layer is reduced, so that the liquid crystal molecules are aligned largely shifted from homeotropic alignment when no voltage is being applied. This causes the light transmittance (light leakage) to increase, deteriorating the black state when no voltage is being applied.

Phase Difference Plate

In the case where a vertically aligned liquid crystal molecules are disposed between two polarizing plates whose optical axes are orthogonal to each other, a satisfactory black state with a high contrast is obtained in the front surface direction. However, when the device is observed from a different viewing angle, a contrast ratio is decreased due to light leakage, depending upon (i) the viewing angle dependence of characteristics of the polarizing plates and (ii) the viewing angle dependence of retardation of a liquid crystal layer (the retardation of the vertically aligned liquid crystal molecules is changed depending upon the direction). This phenomenon occurs particularly in the 45° direction from the polarization axis (azimuth angle, i.e., intra-substrate angle). In order to prevent this phenomenon, it is effective to decrease the retardation of the vertically aligned liquid crystal molecules. Alternatively, it is preferable that a phase difference plate having a negative uniaxial "Frisbee-type" refractive oval body is disposed between the liquid crystal cell and the polarizing plate. A biaxial phase difference film having the relationship in which the refractive index $n_{x,y}$ in an intra-display surface direction is greater than the refractive index $n_z$ in a direction vertical to a display surface may be used. It is preferable that the phase difference of this phase difference plate is smaller than the retardation peculiar to the liquid crystal cell determined by the product of $\Delta n$ peculiar to the liquid crystal material and a thickness d of the liquid crystal layer. More preferably, the retardation peculiar to the liquid crystal cell is in the range of about 30% to about 80%. When the retardation is less than about 30%, the effect of the phase difference plate is small. When the retardation is more than about 80%, staining becomes large in the wide viewing angle direction, which is not preferable.

Homeotropic Alignment Layer

As the homeotropic alignment layer, any layers having the surface capable of vertically aligning liquid crystal molecules may be used. The homeotropic alignment layer can be made of an inorganic material or an organic material. For example, polyimide-type materials (JALS-204, produced by Japan Synthetic Rubber Co., Ltd.; 1211, produced by Nissan Chemical Industries, Ltd.), inorganic materials (EXP-OA003; produced by Nissan Chemical Industries, Ltd.), and the like can be used.

Embodiment 2

Figure 7:
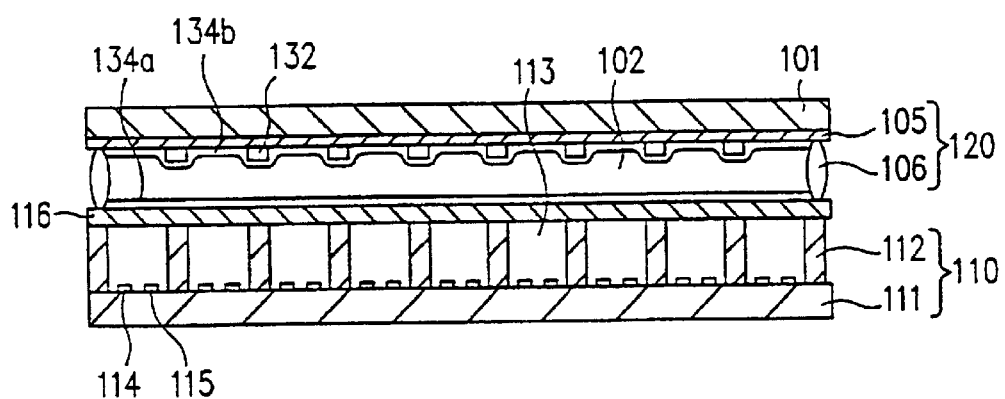
FIG. 7 is a schematic cross-sectional view illustrating an embodiment of a PALC of the present invention.

The present invention is also applicable to a PALC. FIG. 7 is a schematic cross-sectional view of a PALC 400 in the present embodiment. The PALC 400 includes a counter substrate 120, a plasma substrate 110, and a liquid crystal layer 102 disposed therebetween. The liquid crystal layer 102 is sealed with a sealant 106. The plasma substrate 110 includes a substrate 111, a dielectric sheet 116 opposing the substrate 111, and a plurality of plasma chambers 113 defined by partition walls 112 provided between the substrate 111 and the dielectric sheet 116. The plasma chambers 113 oppose the liquid crystal layer 102 with the dielectric layer 116 disposed therebetween. Gas sealed in each plasma chamber 113 is ionized by applying a voltage across an anode 114 and a cathode 115 formed on the surface of the substrate 111 on the plasma chamber 113 side, whereby plasma discharge occurs. A plurality of chambers 113 extend in the shape of stripes in a direction vertical to the drawing surface of FIG. 7 in such a manner as to be orthogonal to transparent electrodes 105 formed on the surface of the counter substrate 120 on the liquid crystal layer 102 side. Intersections of the plasma chambers 113 and the transparent electrodes 105 define pixel regions. Compared with a simple matrix type liquid crystal display device, the transparent electrodes 105 on the counter substrate 120 correspond to display electrodes (signal electrodes), and the plasma chambers 113 correspond to scanning electrodes.

Convex portions 132 in the shape of a lattice are formed on the counter substrate 120 on the liquid crystal layer 102 side so as to correspond to the non-pixel regions. The convex portions 132 allow axis-symmetrically aligned regions to be formed so as to correspond to the pixel regions. Furthermore, homeotropic alignment layers 134a and 134b are provided on the surfaces of the plasma substrate 110 and the counter substrate 120 on the liquid crystal layer 102 side.

The basic operation, the convex portions defining the pixel regions, the control of the positions of central axes in axis-symmetrical alignment, the liquid crystal material, the photocurable resin, the phase difference plate, and the homeotropic alignment layer are basically the same as described in Embodiment 1. Therefore, the detailed descriptions thereof will be omitted here. The unique characteristics of the PALC will be described below.

In the case of the PALC according to the present invention, regarding $\Delta\epsilon$ of the liquid crystal material, $\epsilon_{//}$ is preferably as small as possible because voltage can be easily applied to the liquid crystal layer. More specifically, $\epsilon_{//}$ is preferably in the range of 2.5 to 3.3. (Here, $\Delta\epsilon$ is defined as a difference between $\epsilon_{//}$ and $\epsilon_\perp$. $\epsilon_{//}$ is the component of the dielectric constant parallel to the direction of orientation vector of the liquid crystal molecules, and $\epsilon_\perp$ is the component of the dielectric constant perpendicular thereto.)

Regarding the solid dielectric layer, a voltage to be applied to the liquid crystal layer 102 is divided between the liquid crystal layer 102 and the dielectric sheet 116 in accordance with the capacitance (see FIG. 7). In general, in the case of the PALC, the thickness of the dielectric sheet 116 is larger than that of the liquid crystal layer 102, so that a voltage applied to the liquid crystal layer 102 is smaller than that applied to the dielectric sheet 116. Thus, the effect of the voltage drop caused by the formation of a solid dielectric layer on the surface of the dielectric sheet 116 on the liquid crystal layer 102 side is relatively small, so that the formation of a solid dielectric layer with a thickness of about several um does not cause any practical problems.

Arrangement of Polarizing Plates

Figure 8A:
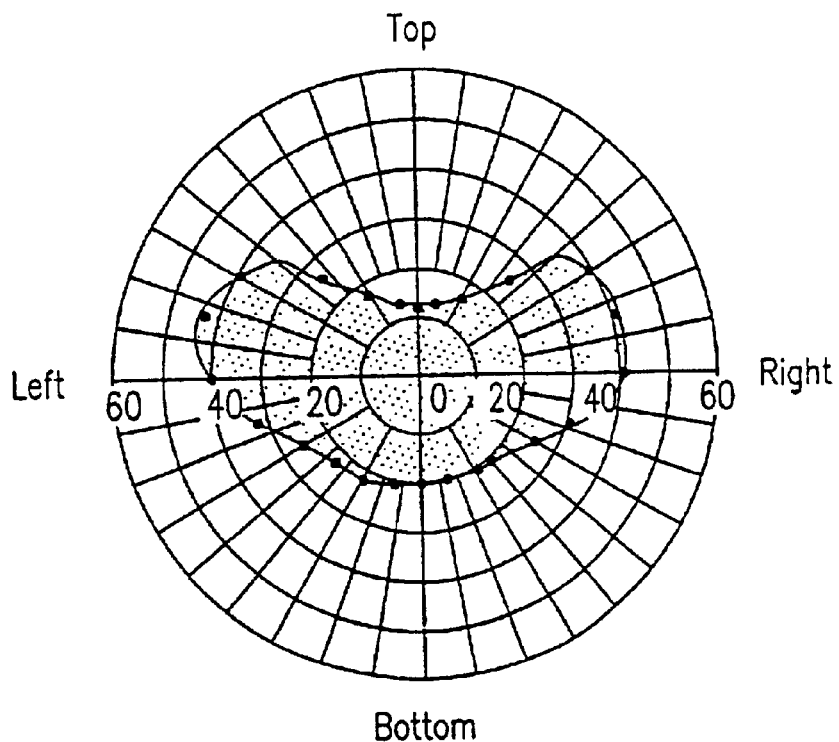
FIG. 8A is a radar chart showing viewing angle characteristics of a liquid crystal display device in a TN mode.
Figure 8B:
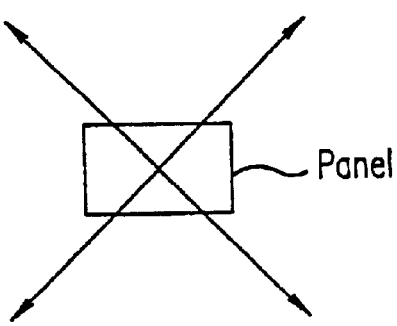
FIG. 8B is a schematic view illustrating the arrangement of polarizing plates in the liquid crystal display device in a TN mode.
Figure 9:
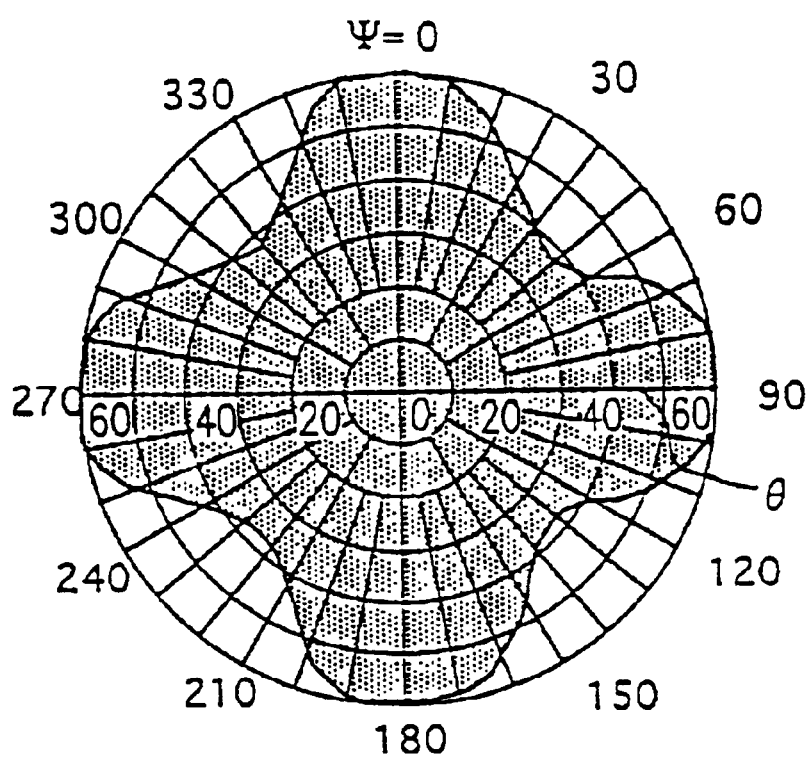
FIG. 9 is a radar chart showing viewing angle characteristics of a PALC of the present invention.

When there is a difference in refractive index on an attachment surface between the plasma substrate and the thin glass sheet (i.e., the dielectric sheet), light leaks from the attachment surface due to the birefringence and the difference in refractive index with respect to polarized light, whereby the attachment portion becomes visible. This phenomenon becomes most obvious in the case where the angle between the polarization axes of the polarizing plates and the surface having the difference in refractive index is 45°. In the case where this angle is 0° or 90°, this phenomenon becomes minimum. In the case of a device in a TN mode, in order to widen the viewing angle in the sideward direction as seen by an observer, considering its viewing angle characteristics (FIG. 8A), the polarizing plates are generally disposed in such a manner that the polarization axes are tilted by 45° from the crosswise direction on the display surface as shown in FIG. 8B. When the polarizing plates of the PALC in a TN mode are disposed in this way, since the plasma chamber structure causing the difference in refractive index extends in the ordinate or abscissa direction of the display surface, the plasma chamber structure is easily visualized. However, the axis-symmetrical alignment mode (vertical ASM mode) used in the present invention has viewing angle characteristics with high symmetry, as shown in FIG. 9; therefore, the polarization axes of the polarizing plates can be disposed in a crosswise direction of the display surface, whereby the plasma chamber structure can be made invisible. In this respect, there is an advantage that the axis-symmetrical alignment is applied to the PALC.

Embodiment 3

Basic Structure and Operation Principle

In the present embodiment, the case where concave portions or through-holes (hereinafter, referred to as axis-symmetrical alignment central axis forming portions) for axis-symmetrically aligning liquid crystal molecules are provided at predetermined positions (preferably, substantially central portions of the pixel regions) of electrodes on at least one substrate will be described.

Figure 10A:
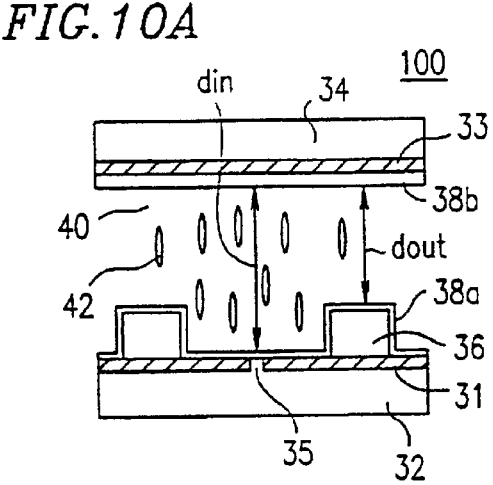
FIGS. 10A through 10D are schematic views illustrating the basic structure and operation principle of a liquid crystal display device in another embodiment of the present invention.
Figure 10B:
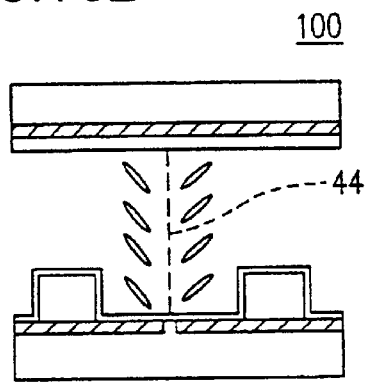
Figure 10C:
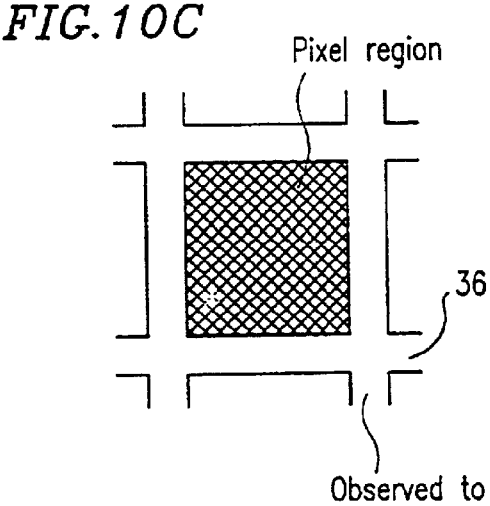
Figure 10D:
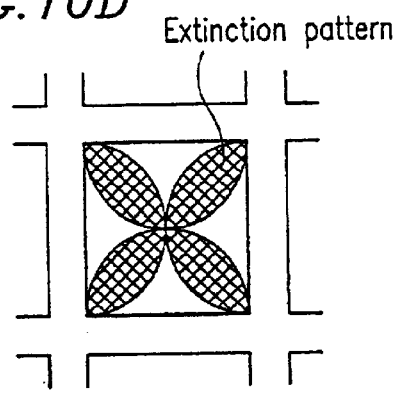

Referring to FIGS. 10A through 10D, the basic structure and operation principle of a liquid crystal display device 100 in the present embodiment will be described. FIG. 10A is a schematic cross-sectional view of the liquid crystal display device 100 when no voltage is being applied, and FIG. 10B is a schematic cross-sectional view thereof under the application of a voltage. FIG. 10C shows results obtained by observing the upper surface of the liquid crystal display device 100 shown in FIG. 10A with a polarizing microscope in crossed-Nicols, and FIG. 10D shows results obtained by observing the upper surface of the liquid crystal display device 100 shown in FIG. 10B with a polarizing microscope in crossed-Nicols.

The liquid crystal display device 100 includes a liquid crystal layer 40 containing a liquid crystal material (liquid crystal molecules) 42 with a negative dielectric anisotropy $\Delta\epsilon$ between a pair of substrates 32 and 34. Transparent electrodes 31 and 33 are provided on the surfaces of the substrates 32 and 34 on the liquid crystal layer 40 side, respectively. Homeotropic alignment layers 38a and 38b are provided on the transparent electrodes 31 and 33, respectively. Furthermore, an axis-symmetrical alignment central axis forming portion 35 is provided at a predetermined position (preferably, a substantially central portion of each pixel region) of each of the electrodes (electrodes 31 in FIG. 10A) on at least one substrate. Convex portions 36 are formed on the surface of at least one of the substrates 32 and 34 (substrate 32 in FIG. 10A) on the liquid crystal layer 40 side.

Because of the convex portions 36, the liquid crystal layer 40 has two different thicknesses $d_{out}$ and $d_{in}$. As a result, upon the application of a voltage for forming axis-symmetrical alignment central axes (described later), liquid crystal regions exhibiting axis-symmetrical alignment are defined by the convex portions 36. The formation of the convex portions 36 defines the positions and sizes of the liquid crystal regions exhibiting axis-symmetrical alignment. The detail of the convex portions 36 is as described in Embodiment 1. Furthermore, the position of each axis-symmetrical alignment central axis is controlled by the axis-symmetrical alignment central axis forming portion 35. Thus, as shown in FIG. 10C, the liquid crystal molecules 42 are axis-symmetrically aligned around an axis-symmetrical alignment central axis 44 formed in the axis-symmetrical alignment central axis forming portion 35 in the pixel region defined by the convex portions 36.

The liquid crystal molecules 42 are aligned in a direction vertical to the substrates 32 and 34 by an alignment regulating force of the hemeotropic alignment layers 38a and 38b when no voltage is being applied as shown in FIG. 10A. When the pixel regions are observed with a polarizing microscope in crossed-Nicols when no voltage is being applied, a dark field of view (normally black mode) is exhibited as shown in FIG. 10C. Upon the application of a voltage, the liquid crystal molecules 42 having a negative dielectric anisotropy $\Delta\epsilon$ are provided with a force which aligns the major axes of the liquid crystal molecules 42 in a direction vertical to the electric field direction. Therefore, the liquid crystal molecules 42 are tilted from the direction vertical to the substrates as shown in FIG. 10D (gray-scale display state). When the pixel regions in this state are observed with a polarizing microscope in crossed-Nicols, extension patterns are observed in the directions of polarization axes.

FIG. 2 shows a voltage-transmittance curve of the liquid crystal display device of the present invention. The abscissa axis represents a voltage, and the ordinate axis represents a relative transmittance. As shown in FIG. 2, when a voltage is increased, the transmittance gradually increases. When the voltage is further increased, the transmittance further increases to reach saturation.

When a voltage is increased from the non-application state, the liquid crystal molecules 42 are tilted from a direction vertical to the substrates 32 and 34. However, the direction in which the liquid crystal molecules 42 are tilted is not uniquely determined. According to the present invention, because of the convex portions 36, a plurality of central axes in axis-symmetrical alignment (hereinafter, merely referred to as "central axes") are formed in liquid crystal regions exhibiting axis-symmetrical alignment defined by the convex portions 36. However, when such a plurality of central axes are present, both the alignment and the transmittance are unstable.

When a voltage of $\frac{1}{2} V_{th}$ or more is continued to be applied, a plurality of central axes become a single central axis in each liquid crystal region defined by the convex portions 36. In the case where a voltage applied to the liquid crystal layer 40 is between $\frac{1}{2} V_{th}$ and $V_{st}$, the transmittance reversibly changes in the operation range as shown in FIG. 2. Under the condition that a voltage in the vicinity of $\frac{1}{2} V_{th}$ is applied, the liquid crystal molecules are aligned in a direction almost vertical to the substrates, while remembering the axis-symmetrical alignment state under the application of a voltage of $\frac{1}{2} V_{th}$ or more, i.e., the symmetry with respect to the central axis. However, when the voltage is removed or the voltage is decreased to less than $\frac{1}{2} V_{th}$, the liquid crystal molecules are aligned in a direction almost vertical to the substrates and return to a state not remembering the axis-symmetrical alignment state. Thus, even when a voltage exceeding $\frac{1}{2} V_{th}$ is applied again, a plurality of central axes are once again formed. For example, at a stage where an n-type liquid crystal material is injected into a liquid crystal cell, the liquid crystal molecules behave in the same way as in the case of an applied voltage of less than ½ $V_{th}$.

As described above, the liquid crystal display device of the present invention operates in a normally black mode in which the liquid crystal molecules are aligned in a direction vertical to the substrates to perform a black display when no voltage is being applied, and the liquid crystal molecules are axis-symmetrically aligned around a central axis formed in each pixel region to perform a white display under the application of a voltage. However, a plurality of central axes are formed after the application of a voltage, so that the operation becomes unstable with a black display being performed when no voltage is being applied. In order to achieve a stable operation in the display mode of the present invention, it is desirable that one central axis is formed in each pixel region prior to a display operation.

In order to form one central axis in each pixel region before the display operation, a predetermined voltage, i.e., a voltage of ½ $V_{th}$ or more should be applied. Thus, one central axis is formed in each pixel region, whereby a stable axis-symmetrical alignment state can be realized during a white display. However, the removal of the voltage allows a plurality of central axes to be formed as in an initial unstable state. Therefore, the device should be used under the application of a predetermined voltage, i.e., a voltage in the vicinity of ½ $V_{th}$ without removing the voltage even during a black display after the commencement of a display. In the display mode of the present invention, the device is preferably used in the range of a voltage at which a stable axis-symmetrical alignment state is obtained, i.e., in the range of ½ $V_{th}$ to $V_{st}$.

To form one central axis in each pixel region before the display operation for the purpose of obtaining a stable operation state is referred to as "axis-symmetrical alignment central axis forming process". A voltage applied for the purpose of forming central axes is referred to as "axis-symmetrical alignment central axis forming voltage".

Control of the Positions of Central Axes

As described above, according to the present invention, the liquid crystal molecules are aligned in a direction vertical to the substrates when no voltage is being applied. When a voltage is continued to be applied, the liquid crystal molecules are axis-symmetrically aligned around one central axis in each liquid crystal region defined by the convex portions. Thus, a liquid crystal display device with a high contrast and a wide viewing angle can be realized.

However, since the direction in which the liquid crystal molecules are tilted under the application of a voltage is not uniquely determined, the central axes can be formed at arbitrary positions, depending upon the pixel region. For example, there is a possibility that the central axis is formed at different positions even in the identical pixel region every time a voltage is applied. Alternatively, there is a possibility that even if an identical voltage is simultaneously applied, an axis-symmetrical alignment central axis forming voltage may be applied to the liquid crystal molecules in various manners depending upon the pixel region, whereby the central axes are formed at different positions, depending upon the pixel region.

When the positions at which the central axes are formed vary depending upon the pixel region, there is a great effect on display quality. The relationship between the positions of the central axes and the display quality is as described with reference to FIGS. 3A through 3D. More specifically, in the case where the central axis 44 is formed at each central position in the pixel regions as shown in FIG. 3A, all the pixel regions are observed in a similar manner even when the display surface is observed with a cell tilted as shown in FIG. 3C. In the case where some central axes are formed shifted from central portions of the pixel regions as shown in FIG. 3B, the pixel regions with the central axes shifted are observed in a different manner from the other pixel regions as shown in FIG. 3D, so that a nonuniform (rough) display is obtained. This problem becomes serious particularly in a gray-scale display.

In order to obtain a display without any roughness, it is preferable that the positions of the central axes are controlled by conducting an axis-symmetrical alignment central axis forming process prior to performing a display. Regions where the liquid crystal molecules keep a homeotropic alignment state even under the application of a voltage are provided in the pixel regions by the axis symmetrical alignment central axis forming process, whereby the positions of the central axes can be controlled. The regions where the liquid crystal molecules keep a homeotropic alignment state even under the application of a voltage can be provided by forming axis-symmetrical alignment central axis forming portions in the electrodes in the pixel regions. In this case, it is preferable that Sa satisfies 0%<Sa/A<about 4%, where Sa is an area of a region where the liquid crystal molecules are aligned in a direction vertical to the substrates under the application of an axis-symmetrical alignment central axis forming voltage in each pixel region, and A is an area of each pixel region, for the following reason. When Sa is 0, there is no effect of controlling the positions of the central axes. When Sa is about 4% or more, the ratio of the axis-symmetrical alignment central axis forming portions which do not contribute to a display is too large, and those portions become black defects, decreasing the contrast in most cases.

The liquid crystal molecules in the axis-symmetrical alignment central axis forming portions are stable without the alignment state thereof being influenced by an electric field. Furthermore, even when a central axis is formed in a position of the pixel region other than the portion where the liquid crystal molecules keep a homeotropic alignment state even under the application of a voltage, the central axis moves from the portion where it is originally formed to the portion where the liquid crystal molecules keep a homeotropic alignment state by continuing to apply an axis-symmetrical alignment central axis forming voltage. Thus, the central axis is formed in the portion of the pixel region where the liquid crystal molecules keep a homeotropic alignment state even under the application of a voltage. The time required to allow the central axis to move to a predetermined position (i.e., a portion where the liquid crystal molecules keep a homeotropic alignment state even under the application of a voltage) should be prescribed to be, for example, tens of seconds or more. Furthermore, the application of an axis-symmetrical alignment central axis forming voltage while heating a liquid crystal cell facilitates the movement of the central axis from the portion where the axis is originally formed to the portion where the liquid crystal molecules keep a homeotropic alignment state, as a result of which the controllability of the positions of the central axes are furthermore improved.

Figure 11A:
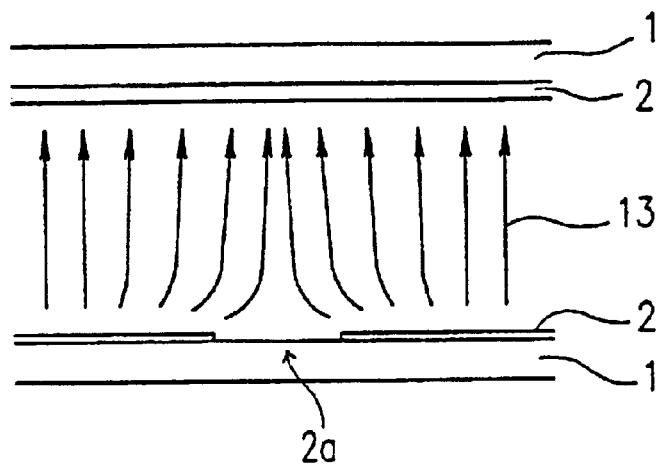
FIG. 11A is a schematic view showing a state of an electric field distribution when a voltage is applied to the liquid crystal display device in the embodiment of the present invention.
Figure 11B:
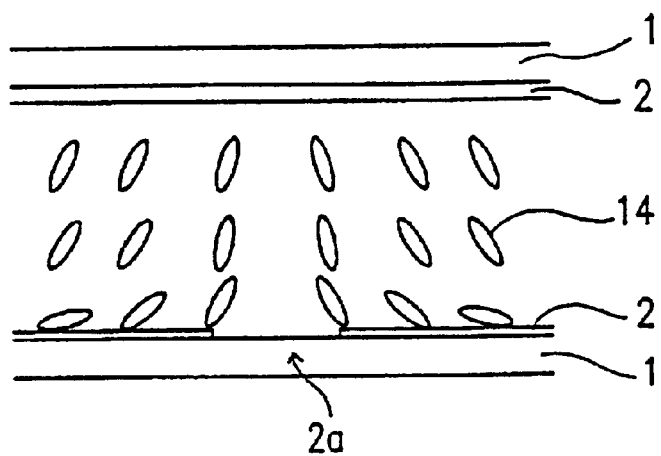
FIG. 11B is a schematic view showing an alignment state of liquid crystal molecules when a voltage is applied to the liquid crystal display device shown in FIG. 11A.

Alternatively, by providing an axis-symmetrical alignment central axis forming portion at a predetermined position (preferably, a substantially central portion of each pixel region) of each electrode in the pixel regions, the positions of the central axes can be controlled. FIGS. 11A and 11B show the states of the electric force and the alignment of the liquid crystal molecules under the application of a voltage to a liquid crystal cell in which an axis-symmetrical alignment central axis forming portion is provided in a pixel region. In these figures, the reference numeral 1 denotes substrates, 2 denotes electrodes, 2a denotes an axis-symmetrical alignment central axis forming portion, 13 denotes an electric force, and 14 denotes liquid crystal molecules.

An electric field in the vicinity of the boundary between the axis-symmetrical alignment central axis forming portion 2a and the electrode 2 is strained by providing the axis-symmetrical alignment central axis forming portion 2a, and as shown in FIG. 11A, an electric force 13 having a component parallel to the substrates is generated. Consequently, as shown in FIG. 11B, the liquid crystal molecules in the pixel region are influenced by the strained electric field, and even when the central axis is formed in a portion of the pixel region not corresponding to the axis-symmetrical alignment central axis forming portion 2a, the central axis moves from the portion where the axis is originally formed to a portion of the pixel region corresponding to the axis-symmetrical alignment central axis forming portion 2a. Thus, the axis-symmetrical alignment central axis is formed in the portion of the pixel region corresponding to the axis-symmetrical alignment central axis forming portion 2a.

Alternatively, the positions of the central axes can be controlled by adjusting the thickness of the liquid crystal layer in the pixel region. The adjustment of the thickness of the liquid crystal layer in the pixel region is as described in Embodiment 1 with reference to FIGS. 4A and 4B.

Stabilization of an Axis-symmetrical Alignment State of the Liquid Crystal Molecules under the Application of an Axis-symmetrical Alignment Central Axis Forming Voltage In order to perform a stable display operation in a display mode of the present invention, it is desirable that an axis-symmetrical alignment state is stabilized by forming one central axis in each pixel region prior to a display operation. For this purpose, as described above, the axis-symmetrical alignment central axis forming process should be conducted, in which a predetermined voltage is applied prior to the display operation. Furthermore, it is preferable that a predetermined voltage is applied even during a black display after the commencement of the display operation, and the operation voltage, for example, in the range of ½ $V_{th}$ to $V_{st}$, capable of obtaining a stable axis-symmetrical alignment state is used. The reason for applying a predetermined voltage even during a black display is that the liquid crystal molecules are allowed to remember an axis-symmetrical alignment state (i.e., symmetry with respect to a central axis) formed upon the application of a voltage of ½ $V_{th}$ or more so as not to return to the initial state. The axis-symmetrical alignment central axis forming process may be conducted every time before the commencement of the display operation after the completion of a liquid crystal display device, or may be included in the course of the production of a liquid crystal display device.

Axis-Symmetrical Alignment Fixing Layer

According to the present invention, when no voltage is being applied, the liquid crystal molecules may be prescribed to assume an axis-symmetrical alignment state similar to that under the application of a voltage in the vicinity of ½ $V_{th}$. In order to realize this, the axis-symmetrical alignment fixing layer can be formed on the surface of at least one of the substrates on the liquid crystal layer side. By forming the axis-symmetrical alignment fixing layer, an axis-symmetrical pretilt angle can be provided to liquid crystal molecules in each liquid crystal region exhibiting axis-symmetrical alignment even under the condition that a voltage of ½ $V_{th}$ or more is not applied. Although the liquid crystal molecules are provided with a pretilt angle by the axis-symmetrical alignment fixing layer even when no voltage is being applied, the tilt of the liquid crystal molecules from a direction normal to the substrates is small, and a black level is substantially equal to that in the case without the axis-symmetrical alignment fixing layer.

The axis-symmetrical alignment fixing layer can be formed by a method including the steps of disposing a precursor mixture containing at least a liquid crystal material and a photocurable material between a pair of substrates, and curing the photocurable material in the mixture. The photocurable material is cured, for example, by exposing the precursor mixture disposed between the substrate to light under the application of an axis-symmetrical alignment central axis forming voltage. Any appropriate light exposure conditions can be adopted. A thermosetting material can be used in place of the photocurable material. In the case of using the thermosetting material, any appropriate curing conditions (heating conditions) can be adopted. The content of the curable material in the precursor mixture is as described in Embodiment 1.

The photocurable material is preferably used for the following reason. Desired regions of the photocurable material can be selectively cured, using a photomask or the like, so that liquid crystal regions (polymer regions) are likely to be formed in a regular manner in terms of space. If materials transmitting light with a desired wavelength are used for transparent electrodes and color filters in a liquid crystal display device, these members can be used in place of a photomask. The use of the members of the liquid crystal display device as a photomask has the advantage in that the liquid crystal regions can be formed in a self-matching manner.

In order for the axis-symmetrical alignment fixing layer to provide an axis-symmetrical pretilt angle to the liquid crystal molecules in each liquid crystal region exhibiting axis-symmetrical alignment when no voltage of ½ $V_{th}$ or more is being applied, it is desirable that the liquid crystal molecules are tilted at a certain angle with respect to a direction normal to the substrates in the course of the formation of the axis-symmetrical alignment fixing layer (that is, it is desirable that the liquid crystal molecules have a tilt angle). In order to tilt the liquid crystal molecules at a certain angle with respect to a direction normal to the substrates, a voltage should be applied. The applied voltage should be, for example, in the range of ½ $V_{th}$ to $V_{st}$ capable of stabilizing axis-symmetrical alignment.

The axis-symmetrical alignment central axis forming voltage can be applied by using the electrodes (31 and 33 in FIG. 10A) which apply a voltage to the liquid crystal layer 40 for performing a display. The axis-symmetrical alignment central axis forming voltage is preferably an AC with a frequency of 1 Hz or more. The reason for using an AC is that the use of a DC may degrade the precursor mixture. When the frequency of the voltage is less than 1 Hz, the liquid crystal molecules become unlikely to follow the changes in voltage, making it impossible to axis-symmetrically align the liquid crystal molecules. In order to tilt the liquid crystal molecules at a certain angle with respect to a direction normal to the substrates, a magnetic field may be applied in place of the axis-symmetrical alignment central axis forming voltage.

EXAMPLES

Hereinafter, the present invention will be described by way of illustrative examples. However, the present invention is not limited thereto.

Example 1

Figure 12A:
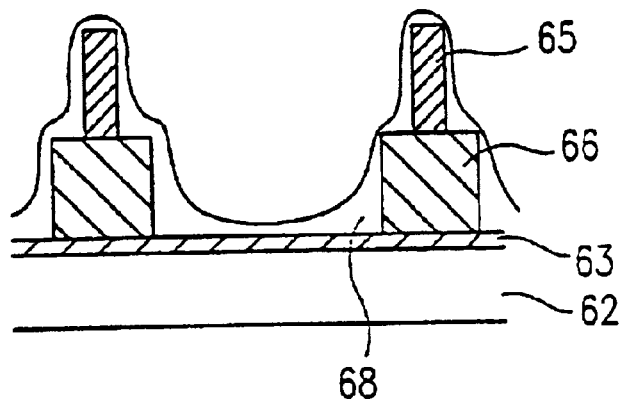
FIG. 12A is a schematic partial cross-sectional view of a substrate used in a liquid crystal display device in Example 1 of the present invention.
Figure 12B:
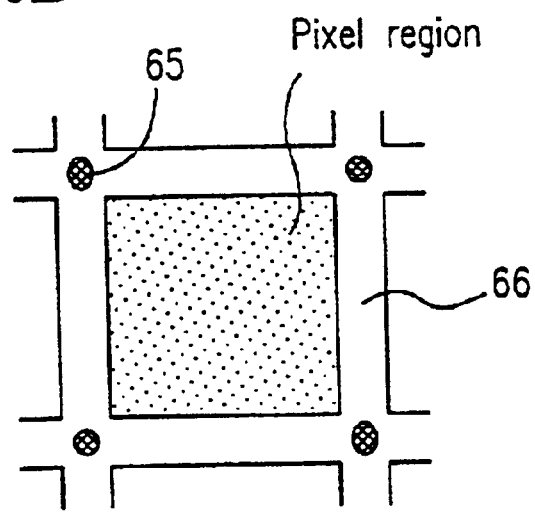
FIG. 12B is a plan view thereof.

Referring to FIGS. 12A and 12B, a method for producing a liquid crystal display device in the present example will be described. Convex portions 66 with a height of about 3 μm were formed with a photoresist (OMR83; produced by Tokyo Ohka-sha) on regions other than pixel regions of a substrate 62 having transparent electrodes 63 made of ITO (thickness: about 100 nm) on its surface. Then, spacers 65 with a height of about 5 μm were formed on the convex portions 66 with photosensitive polyimide. The size of a region (i.e., a pixel region) defined by the convex portions 66 was prescribed to be 100 μm×100 μm. Polyimide (JALS-204; produced by Japan Synthetic Rubber Co., Ltd.) was spin-coated onto the resultant substrate to form a homeotropic alignment layer 68. Furthermore, a homeotropic alignment layer was also formed with the same material on transparent electrodes of the other substrate (not shown). These substrates were attached to each other to complete a liquid crystal cell.

An n-type liquid crystal material ($\Delta\epsilon = -4.0$; $\Delta n = 0.08$; a twist angle peculiar to the liquid crystal material=90° in a cell gap of 5 μm,) was injected into the cell produced as described above, and a voltage of about 7 volts was applied to the cell. Immediately after the application of the voltage, a plurality of central axes are present in an initial state. When the voltage is continued to be applied, one axis-symmetrical alignment region (monodomain) was formed in each pixel region.

Polarizing plates were disposed in crossed-Nicols on both sides of the cell, whereby a liquid crystal display device was produced. The structure of the liquid crystal display device thus obtained was substantially the same as that of the liquid crystal display device 100 shown in FIGS. 1A through 1D, except that the cross-section of the homeotropic alignment layer 68 had the shape of a mortar as shown in FIG. 12A (polarizing plates are not shown). Since the homeotropic alignment layer 68 has a cross-section in the shape of a mortar, a differential coefficient of a curve showing changes in thickness with respect to the position (from a central portion of a pixel to a peripheral portion thereof) is positive, and a differential coefficient of a curve showing changes in thickness of the liquid crystal layer in the pixel region is negative.

The axis-symmetrical alignment of the cell in Example 1 is stable under the application of a voltage of ½ $V_{th}$ or more, and is disturbed when the voltage is decreased to less than ½ $V_{th}$ to return to an initial state. When a voltage is applied to the cell again, an initial axis-symmetrical alignment with a plurality of central axes is obtained. Thereafter, an axis-symmetrical alignment state in which one central axis is formed in each pixel region is obtained. This phenomenon is obtained even when the same experiment is conducted 20 times. After forming the axis-symmetrical alignment state by the application of a voltage of ½ $V_{th}$ or more, the cell in Example 1 was measured for electro-optic characteristics in a voltage range (½ $V_{th}$ or more) in which the axis-symmetrical alignment was stable.

Figure 13:
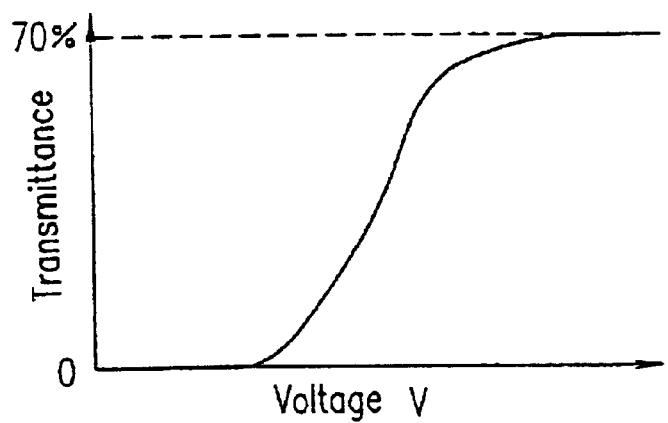
FIG. 13 is a graph showing electro-optic characteristics of the liquid crystal display device in Example 1 of the present invention.
Figure 14:
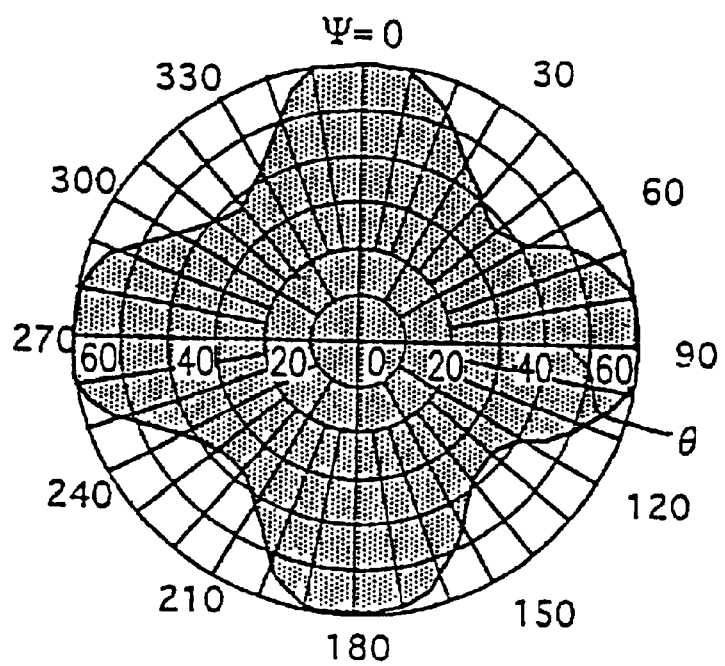
FIG. 14 is a radar chart showing viewing angle characteristics of the liquid crystal display device in Example 1 of the present invention.

FIG. 13 shows the electro-optic characteristics thus obtained. As is apparent from FIG. 13, the liquid crystal display device of the present invention had a satisfactory contrast ratio (CR=300:1, 5 volts) with a low transmittance when no voltage is being applied. Regarding the viewing angle characteristics, a high contrast ratio was obtained in a wide viewing angle range as shown in FIG. 14. In FIG. 14, ψ represents an azimuth angle (i.e., intra-display surface angle), θ represents a viewing angle (i.e., a tilt angle from a normal to the display surface), and the hatched portion represents the region with a contrast of 10:1 or more.

Comparative Example 1

In Comparative Example 1, the homeotropic alignment layer 68 was directly formed on the transparent electrode 63 formed on the surface of the substrate 62 shown in FIG. 12A. Thereafter, the spacers 65 were formed using photosensitive polyimide in the same way as in Example 1. In Comparative Example 1, the convex portions 66 as shown in FIGS. 12A and 12B were not formed. The resultant substrate was attached to the counter substrate obtained in the same way as in Example 1 to produce a liquid crystal cell. The thickness of the liquid crystal layer in the pixel regions in the cell was constant.

When the same material as that in Example 1 was injected into the cell, the liquid crystal molecules were randomly aligned, and disclination lines were formed in a random manner. The cell was observed under the application of a voltage, showing that the display was rough in gray scales.

Example 2

Figure 15:
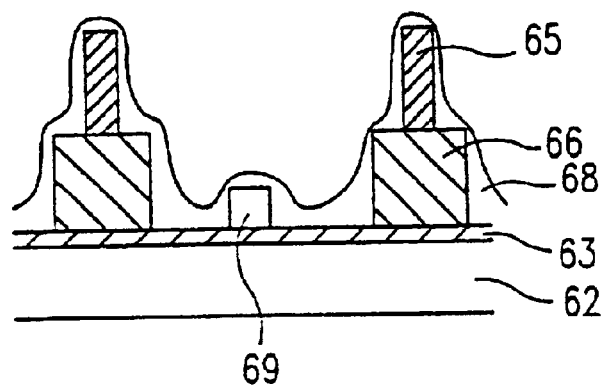
FIG. 15 is a schematic partial cross-sectional view of a substrate used in a liquid crystal display device in Example 2 of the present invention.

As shown in FIG. 15, a projection 69 was formed in a central portion of a pixel region on the substrate 62 having the convex portions 66 in Example 1 using a resist material (OMR83). The width of the projection 69 is preferably about ¹⁄₁₀ or less of that of the pixel region. When the width of the projection 69 exceeds about ¹⁄₁₀ of that of the pixel region, the opening ratio decreases, resulting in a decrease in transmittance in a device, which is not preferable. A liquid crystal cell was produced in the same way as in Example 1, except for providing the projections 69.

As a result of the observation of the cell, a central axis was formed at a position of each projection 69, and thus, a liquid crystal display device in which central axes were formed at central portions in almost all the pixel regions was obtained. When the liquid crystal display device was observed in various viewing angle directions, a display without roughness was obtained.

Examples 3 and 4 and Comparative Examples 2 and 3

Liquid crystal display devices in Examples 3 and 4 and Comparative Examples 2 and 3 were produced in the same way as in Example 1, except that a cell gap (thickness of a liquid crystal layer) was adjusted as shown in Table 1. The adding amount of a chiral agent (S-811: produced by Merck & Co., Inc.) in the liquid crystal material used in each liquid crystal display device was adjusted in such a manner that the twist angle peculiar to the liquid crystal material became 90°.

TABLE 1

|  | Example | | | Comparative Example | |
| --- | --- | --- | --- | --- | --- |
|  | 1 | 3 | 4 | 2 | 3 |
| Cell gap d (μm) | 5 | 4.4 | 5.6 | 3.1 | 6.5 |
| d · Δn (nm) at $V_{max}$ | 400 | 352 | 448 | 248 | 520 |
| Transmittance (%) at $V_{max}$* | 70 | 58 | 73 | 39 | 72** |

*Relative value with a transmittance in parallel Nicols being 100%
**Measured at a maximum transmittance When an increasing voltage was applied to the liquid crystal cell in Comparative Example 3 with a retardation of 520 nm until a maximum transmittance was obtained, a transmittance decreased, and a contrast inversion phenomenon (i.e., a phenomenon occurring when the voltage exceeds $V_{max}$ in FIG. 6) was observed in a gray-scale display. In the liquid crystal display device in Comparative Example 2 with a retardation of less than 300 nm, a transmittance was low. It is understood from the experimental results shown in Table 1 that the product d·Δn (retardation) of Δn (birefringence at the maximum driving voltage) of a liquid crystal material and an average thickness d of a liquid crystal layer is preferably in the range of about 300 to about 500 nm.

Examples 5 and 6 and Comparative Examples 4 and 5

Liquid crystal display devices having different twist angles as shown in Table 2 (Examples 5 and 6 and Comparative Examples 4 and 5) were produced by adjusting the adding amount of a chiral agent (S-811: produced by Merck & Co., Inc.) in the liquid crystal material used in the liquid crystal display device in Example 1. The electro-optic characteristics of the liquid crystal display devices were measured under the application of a voltage at which the transmittance of each device became maximum.

TABLE 2

|  | Example | | | Comparative Example | |
| --- | --- | --- | --- | --- | --- |
|  | 1 | 5 | 6 | 4 | 5 |
| Twist angle (°) | 90 | 50 | 110 | 30 | 120 |
| Transmittance (%) at $V_{max}$* | 70 | 41 | 50** | 35 | 35** |

*Relative value with a transmittance in parallel Nicols being 100%
**A contrast inversion phenomenon occurs when a voltage exceeding a value at which a transmittance becomes maximum is applied It is understood from the results shown in Table 2 that the twist angle under the application of the maximum driving voltage is preferably in the range of 45° to 110°.

Example 7

Figure 16:
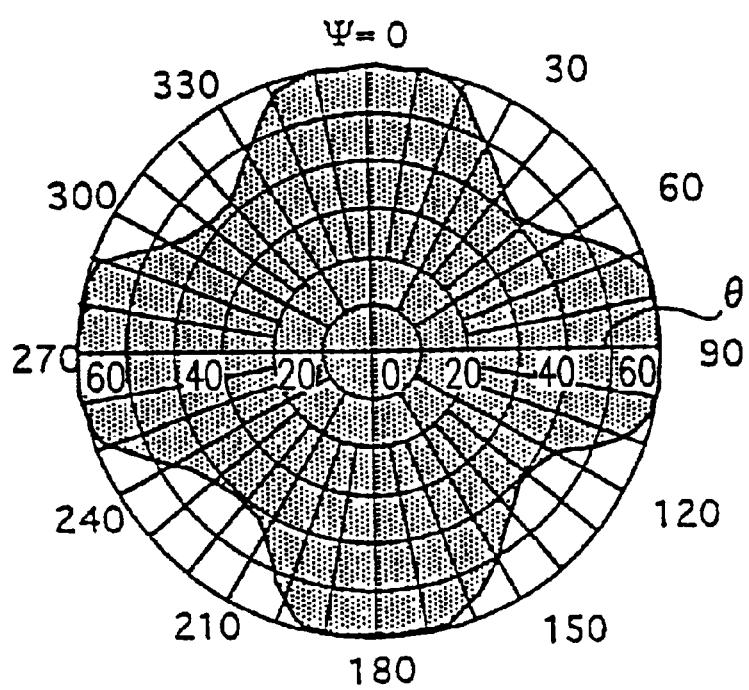
FIG. 16 is a radar chart showing viewing angle characteristics of a liquid crystal display device in Example 7 of the present invention.

A phase difference plate (retardation: 150 nm ascribable to $n_x=n_y$, $n_x-n_z$) having a "Frisbee-type" refractive oval body was placed on one side of the liquid crystal display device in Example 1. FIG. 16 shows the results obtained by measuring the viewing angle characteristics of the liquid crystal display device. It is understood from FIG. 16 that the viewing angle of the liquid crystal display device in Example 7 was wider than that of the liquid crystal display device in Example 1 (see FIG. 14).

Example 8

In the present example, a method for stabilizing axis-symmetrical alignment of liquid crystal molecules by curing a photocurable resin mixed in a liquid crystal material (i.e., by forming an axis-symmetrical alignment fixing layer) will be described.

Figure 17:
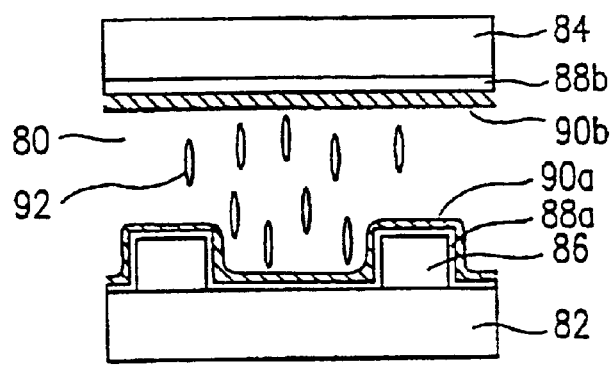
FIG. 17 is a schematic partial cross-sectional view of a liquid crystal display device in Example 8 of the present invention.

FIG. 17 shows a schematic partial cross-sectional view of a liquid crystal display device in Example 8. A liquid crystal display device 200 includes a liquid crystal layer 80 containing an n-type liquid crystal material (liquid crystal molecules) 92 having a negative dielectric anisotropy Δε between a pair of substrates 82 and 84. Homeotropic alignment layers 88a and 88b are provided on the surfaces of the substrates 82 and 84 on the liquid crystal layer 80 side. Convex portions 86 are provided on the surface of at least one of the substrates 82 and 84 on the liquid crystal layer 80 side. The liquid crystal layer 80 has two different thicknesses because of the convex portions 86. Consequently, as described above, liquid crystal regions exhibiting axis-symmetrical alignment are defined by the convex portions 86 under the application of a voltage. In FIG. 17, electrodes formed on the substrates 82 and 84 for applying a voltage to the liquid crystal layer 80 are omitted. The liquid crystal display device 200 is different from the liquid crystal display device 100 in Example 1 in that axis-symmetrical alignment fixing layers 90a and 90b are formed on the homeotropic alignment layers 88a and 88b. The axis-symmetrical alignment fixing layers 90a and 90b allow the liquid crystal molecules in the pixel regions to keep axis-symmetrical alignment even when no voltage is being applied. Therefore, even when a voltage of less than ½ $V_{th}$ is applied (or a voltage is not applied) for driving the liquid crystal display device 200, the electro-optic characteristics as shown in FIG. 2 can be obtained with good reproducibility. The axis-symmetrical alignment fixing layers 90a and 90b keeping axis-symmetrical alignment (pretilt) of the liquid crystal molecules are formed by curing a curable resin mixed in a liquid crystal material under the application of a voltage of ½ $V_{th}$ or more to the liquid crystal layer.

Figure 18:
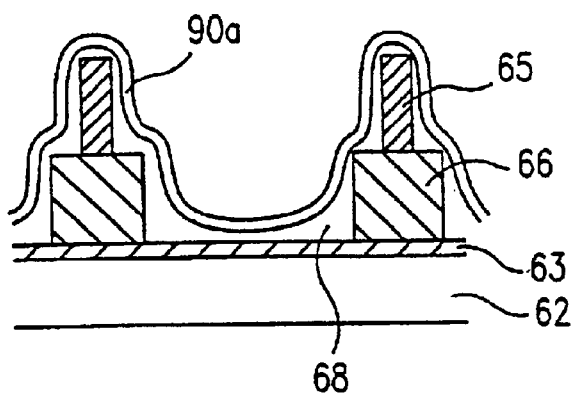
FIG. 18 is a schematic partial cross-sectional view of a substrate used in the liquid crystal display device in Example 8 of the present invention.

Hereinafter, referring to FIG. 18, a method for producing the liquid crystal display device 200 will be described in detail. Convex portions 66 with a height of about 2.5 μm were formed with a photoresist (OMR83; produced by Tokyo Ohka-sha) on regions other than pixel regions of a substrate 62 having transparent electrodes 63 made of ITO (thickness: about 100 nm) on its surface. Then, spacers 65 with a height of about 5 μm were formed on the convex portions 66 with photosensitive polyimide. The size of a region (i.e., a pixel region) defined by the convex portions 66 was prescribed to be 100 μm×100 μm. Polyimide (JALS-204; produced by Japan Synthetic Rubber Co., Ltd.) was spin-coated onto the resultant substrate to form a homeotropic alignment layer 68. Furthermore, a homeotropic alignment layer (not shown) was also formed with the same material on transparent electrodes of the other substrate. These substrates were attached to each other to complete a liquid crystal cell.

In the present example, a mixture containing an n-type liquid crystal material (Δε=−4.0; Δn=0.08; a chiral angle=90° in a cell gap of 5 μm), about 0.3 wt % of a compound A (photocurable resin) represented by the following Formula I, and about 0.1 wt % of a polymerization initiator (Irgacure 651) was injected into the cell. Thereafter, a voltage of 5 volts was applied to the cell to form axis-symmetrical alignment. An axis-symmetrical alignment region was formed in each pixel region defined by the convex portions 66, and a central axis was formed at a central portion of each pixel region. Then, the cell was irradiated with UV-rays (intensity at 365 nm: about 6 mW/cm$^2$) for 10 minutes at room temperature (25° C.) under the application of a voltage about 0.5 volts higher than a threshold voltage of about 2.0 volts, whereby the photocurable resin in the mixture was cured. As a result, the axis-symmetrical alignment fixing layer 90a was formed so as to cover the homeotropic alignment layer 68. The axis-symmetrical alignment layer 90b (see FIG. 17) was also formed on the counter substrate.

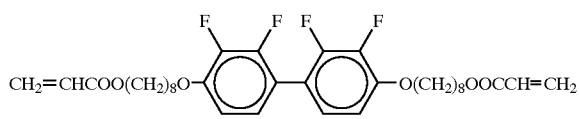

(I)

The axis-symmetrical alignment of the cell in Example 8 did not return to a homeotropic alignment state of the liquid crystal molecules even when a voltage applied to the liquid crystal layer became less than ½ $V_{th}$. It is considered that the pretilt state in axis-symmetrical alignment was kept by the axis-symmetrical alignment fixing layers 90a and 90b. Thus, after the formation of the axis-symmetrical alignment fixing layers 90a and 90b, a phenomenon that a plurality of central axes are present in each pixel region did not occur even when a voltage of ½ $V_{th}$ or more was applied after removal of the voltage applied to the liquid crystal layer, and the homeotropic alignment state (black state) and the axis-symmetrical alignment state (white state) was able to be electrically controlled in a reversible manner. The liquid crystal molecules contained in the liquid crystal layer of the liquid crystal display device in Example 8 were provided with a pretilt angle by the axis-symmetrical alignment fixing layer 90a when no voltage is being applied. However, the shift from the homeotropic alignment was small, so that a black level when no voltage is being applied was substantially equal to that of the liquid crystal display device in Example 1. The electro-optic characteristics and viewing angle characteristics were the same as shown in FIGS. 13 and 14. Although a photocurable resin was used in the present example, a thermosetting resin can also be used.

By providing a phase difference plate having a "Frisbee-type" refractive oval body in the same way as in Example 7, wide viewing angle characteristics can be obtained as shown in FIG. 16. The phase difference plate particularly improves the viewing angle characteristics in a direction at an angle of 45° from polarization axes of polarizing plates.

Examples 9 and 10 and Comparative Examples 6 and 7

Liquid crystal display devices in Examples 9 and 10 and Comparative Examples 6 and 7 were produced in the same way as in Example 8, by injecting the mixtures with varying content of the above-mentioned compound A. As is apparent from the results of Comparative Example 6, when the content of the photocurable resin was less than about 0.1 wt %, the axis-symmetrical alignment was not be able to be fixed effectively. When the content was more than about 6 wt %, the homeotropic alignment of the liquid crystal molecules was disturbed, and light leakage became large when no voltage is being applied. Thus, it is understood that the content of the photocurable resin is preferably in the range of about 0.1 wt % to about 6 wt %.

TABLE 3

|  | Example | | | Comparative Example | |
|---|---|---|---|---|---|
|  | 8 | 9 | 10 | 6 | 7 |
| Content of Compound A (wt %) | 0.3 | 0.1 | 2 | 0.05 | 6 |

TABLE 3-continued

|  | Example | | | Comparative Example | |
|---|---|---|---|---|---|
|  | 8 | 9 | 10 | 6 | 7 |
| Transmittance when no voltage is being applied (%) | 0.06 | 0.04 | 0.1 | 0.03 | 3.2 |
| Fixing of axis-symmetrical alignment | Good | Good | Good | Poor | Good |

Example 11

FIG. 7 is a cross-sectional view of a PALC 400 in the present example. The PALC 400 includes a counter substrate 120, a plasma substrate 110, and a liquid crystal layer 102 disposed therebetween. The liquid crystal layer 102 is sealed with a sealant 106. The plasma substrate 110 includes a substrate 111, a dielectric sheet 116 opposing the substrate 111, and a plurality of plasma chambers 113 defined by partition walls 112 provided between the substrate 111 and the dielectric sheet 116. The plasma chambers 113 oppose the liquid crystal layer 102 with the dielectric layer 116 disposed therebetween. Gas sealed in each plasma chamber 113 is ionized by applying a voltage across an anode 114 and a cathode 115 formed on the surface of the substrate 111 on the plasma chamber 113 side, whereby plasma discharge occurs. A plurality of chambers 113 extend in the shape of stripes in a direction vertical to the drawing surface of FIG. 7 in such a manner as to be orthogonal to transparent electrodes 105 formed on the surface of the counter substrate 120 on the liquid crystal layer 102 side. Intersections of the plasma chambers 113 and the transparent electrodes 105 define pixel regions.

Convex portions 132 in the shape of a lattice are formed on the counter substrate 120 on the liquid crystal layer 102 side so as to correspond to the non-pixel regions. The convex portions 132 allow axis-symmetrically aligned regions to be formed so as to correspond to the pixel regions. Furthermore, homeotropic alignment layers 134a and 134b are provided on the surfaces of the plasma substrate 110 and the counter substrate 120 on the liquid crystal layer 102 side.

The PALC 400 was produced as follows.

A plurality of electrodes each including a pair of anode 114 and cathode 115, and the partition walls 112 with a height of about 200 μm were formed with glass paste so as to make a partition between the adjacent electrodes. Next, a thin film glass substrate 116 with a thickness of about 50 μm was attached to the partition walls 112 with a photocurable sealant. Thereafter, argon gas was sealed into the plasma chambers 113. The entire surface of the thin film glass substrate 116 was spin-coated with JALS-204 (produced by Japan Synthetic Rubber Co., Ltd.) to form the homeotropic alignment layer 134a, whereby the plasma substrate 110 was obtained.

Figure 19A:
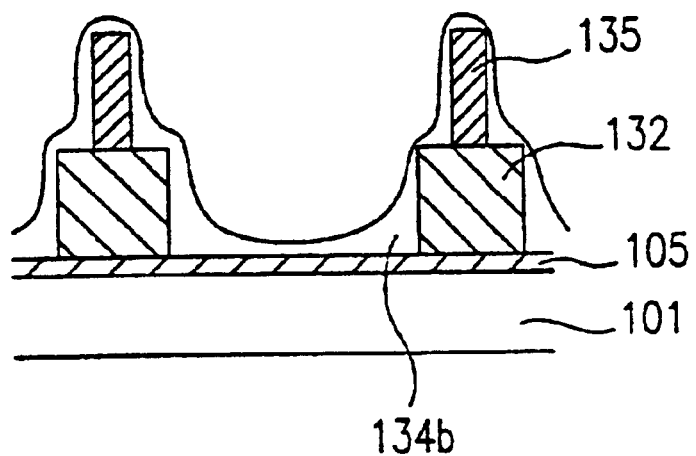
FIG. 19A is a schematic partial cross-sectional view of a substrate used in a PALC in Example 11 of the present invention.
Figure 19B:
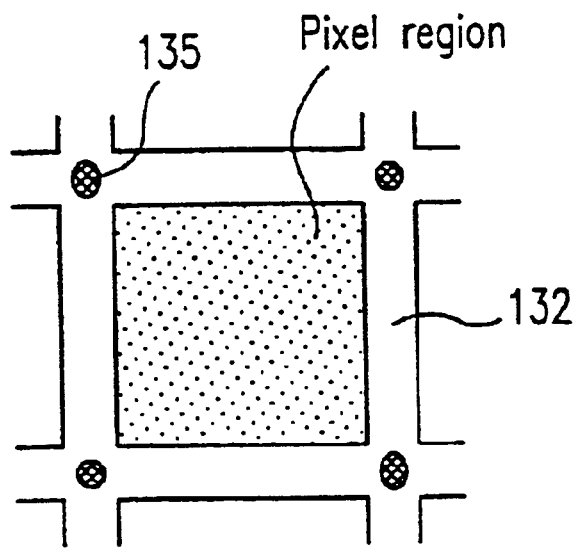
FIG. 19B is a plan view thereof.

Referring to FIGS. 19A and 19B, a method for producing the counter substrate 120 will be described. The convex portions 132 with a height of about 2.7 μm were formed with OMR83 (produced by Tokyo Ohka-sha) on regions other than the pixel regions on a glass substrate 101 having transparent electrodes 105 made of ITO (thickness: about 150 nm) in the shape of stripes. The size of each pixel region was prescribed to be 100 μm×100 μm. Furthermore, spacers 135 with a height of about 6 μm were formed with photosensitive polyimide. The resultant substrate was spin-coated with JALS-204 (produced by Japan Synthetic Rubber Co., Ltd.) to form the homeotropic alignment layer 134b, whereby the counter substrate 120 was obtained. The plasma substrate 110 was attached to the counter substrate 120 to produce a liquid crystal cell.

An n-type liquid crystal material (Δε=−4.0, Δn=0.077; a twist angle peculiar to the liquid crystal material=90° in a cell gap of 6 μm) was injected into the cell. A voltage of about 7 volts was applied to the cell. After application of the voltage, a plurality of central axes were present in an initial state. When the voltage was further continued to be applied, one axis-symmetrically aligned region (monodomain) was formed in each pixel region.

Polarizing plates 161 were disposed in crossed-Nicols on both sides of the cell, whereby a liquid crystal display device was produced. The cross-sectional structure of the liquid crystal layer in the liquid crystal display device thus obtained was substantially the same as that of the liquid crystal display device shown in FIGS. 4A and 4B, except that the cross-section of the homeotropic alignment layer 134b had the shape of a mortar as shown in FIG. 19A (polarizing plates are not shown). Since the homeotropic alignment layer 134b has a cross-section in the shape of a mortar, a differential coefficient of a curve showing changes in thickness with respect to the position (from a central portion of a pixel to a peripheral portion thereof) is positive, and a differential coefficient of a curve showing changes in thickness of the liquid crystal layer in the pixel region is negative.

The axis-symmetrical alignment of the cell in Example 11 was stable under the application of a voltage of ½ $V_{th}$ or more, and was disturbed when the voltage was decreased to less than ½ $V_{th}$ to return to an initial state. When a voltage was applied to the cell again, an initial axis-symmetrical alignment with a plurality of central axes was obtained. Thereafter, an axis-symmetrical alignment state in which one central axis was formed in each pixel region was obtained. This phenomenon was obtained even when the same experiment was conducted 20 times. After forming the axis-symmetrical alignment state by the application of a voltage of ½ $V_{th}$ or more, the cell in Example 11 was measured for electro-optic characteristics in a voltage range (½ $V_{th}$ or more) in which the axis-symmetrical alignment was stable.

FIG. 13 shows the electro-optic characteristics thus obtained. As is apparent from FIG. 13, the liquid crystal display device of the present invention had a satisfactory contrast ratio (CR=300:1, 5 volts) with a low transmittance when no voltage is being applied. The threshold voltage was about 2 volts. A high contrast ratio was obtained in a wide viewing angle range as shown in FIG. 9. In FIG. 9, ψ represents an azimuth angle (i.e., intra-display surface angle), θ represents a viewing angle (i.e., a tilt angle from a normal to the display surface), and the hatched portion presents a region with a contrast of 10:1 or more.

Comparative Example 8

In Comparative Example 8, the homeotropic alignment layer 134b was directly formed on the transparent electrode 105 formed on the surface of the substrate 101 shown in FIG. 19A. Thereafter, the spacers 135 were formed using photosensitive polyimide in the same way as in Example 11. In Comparative Example 11, the convex portions 132 as shown in FIG. 19A were not formed. The resultant counter substrate 120 was attached to the plasma substrate 110 formed in the same way as in Example 11 to produce a liquid crystal cell. The thickness of the liquid crystal layer in the pixel regions in the cell was constant.

When the same material as that in Example 11 was injected into the cell, the liquid crystal molecules were randomly aligned, and disclination lines were formed in a random manner. The cell was observed under the application of a voltage, showing that a display was rough in gray scales.

Example 12

Figure 20:
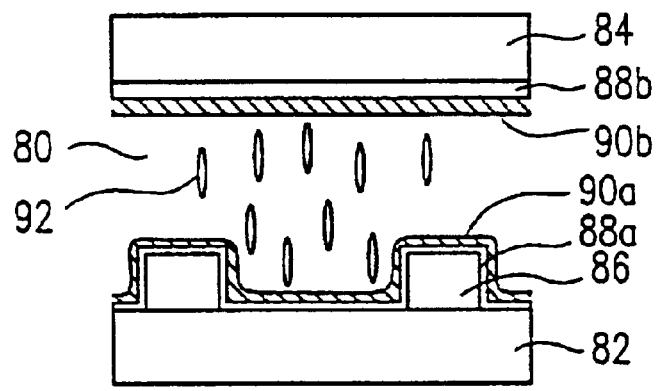
FIG. 20 is a schematic partial cross-sectional view of a PALC in Example 12 of the present invention.

In the present example, a method for stabilizing axis-symmetrical alignment of liquid crystal molecules by curing a photocurable resin mixed in a liquid crystal material will be described. FIG. 20 is a schematic partial cross-sectional view of a liquid crystal display device in Example 12.

The liquid crystal display device 500 includes a liquid crystal layer 80 containing an n-type liquid crystal material (liquid crystal molecules) 92 having a negative dielectric anisotropy Δε between a pair of substrates 82 and 84. A plasma substrate is used as either the substrate 82 or 84. Homeotropic alignment layers 88a and 88b are provided on the surfaces of the substrates 82 and 84 on the liquid crystal layer 80 side. Convex portions 86 are formed on the surface of at least one of the substrates 82 and 84 on the liquid crystal layer 80 side. Since a dielectric sheet provided on the plasma substrate on the liquid crystal layer 80 side is thin, the convex portions are preferably formed on the counter substrate (color filter substrate) in view of the lack of strength of the dielectric sheet.

The liquid crystal layer 80 has two different thicknesses because of the convex portions 86. Consequently, as described above, liquid crystal regions exhibiting axis-symmetrical alignment under the application of a voltage are defined by the convex portions 86. In FIG. 20, electrodes provided on the substrates 82 and 84 for applying a voltage to the liquid crystal layer 80 and plasma chambers are omitted. The liquid crystal display device 500 has the same structure as that of the liquid crystal display device 400 in Example 11, except that the axis-symmetrical alignment fixing layers 90a and 90b are provided on the homeotropic alignment layers 88a and 88b. The axis-symmetrical alignment fixing layers 90a and 90b allow the liquid crystal molecules in the pixel regions to keep axis-symmetrical alignment even when no voltage is being applied. Therefore, even when a voltage of less than ½ $V_{th}$ is applied (or a voltage is not applied) for driving the liquid crystal display device 500, the electro-optic characteristics as shown in FIG. 2 can be obtained with good reproducibility. The axis-symmetrical alignment fixing layers 90a and 90b keeping axis-symmetrical alignment (pretilt) of the liquid crystal molecules are formed by curing a curable resin mixed in a liquid crystal material under the application of a voltage of ½ $V_{th}$ or more to the liquid crystal layer.

Figure 21:
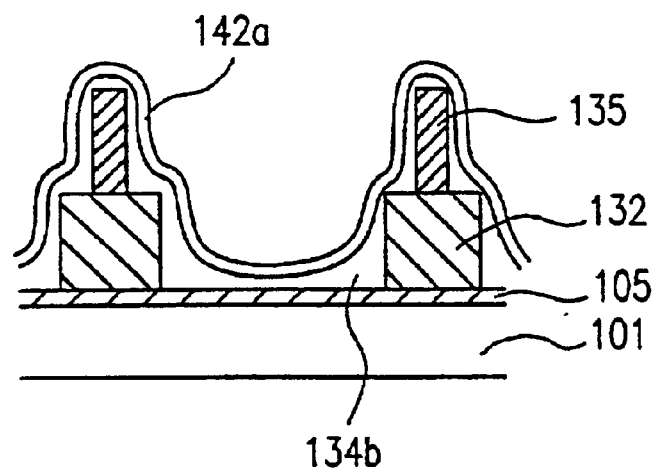
FIG. 21 is a schematic partial cross-sectional view of a substrate used in the PALC in Example 12 of the present invention.

Hereinafter, a method for producing the liquid crystal display device 500 will be described in detail. Referring to FIG. 21, convex portions 132 with a height of about 2.7 μm were formed with a photoresist (OMR83; produced by Tokyo Ohka-sha) on regions other than pixel regions of a substrate 101 having transparent electrodes 105 made of ITO (thickness: 150 nm) on its surface. Then, spacers 135 with a height of about 6 μm were formed on the convex portions 132 with photosensitive polyimide. The size of a region (i.e., a pixel region) defined by the convex portions 132 was prescribed to be 100 μm×100 μm. Polyimide (JALS-204; produced by Japan Synthetic Rubber Co., Ltd.)

was spin-coated onto the resultant substrate to form a homeotropic alignment layer 134b to obtain a counter substrate. Furthermore, a homeotropic alignment layer (not shown) was also formed with the same material on transparent electrodes of the other substrate (plasma substrate). These substrates were attached to each other to complete a liquid crystal cell. This cell was substantially the same as that in Example 11.

In the present example, a mixture containing an n-type liquid crystal material ($\Delta\epsilon=-4.0$; $\Delta n=0.077$; a chiral angle=90° in a cell gap of 6 $\mu$m) and 0.4 wt % of a compound A (light curable resin) represented by the following Formula I, and 0.1 wt % of Irgacure 651 was injected into the cell. Thereafter, a voltage of about 5 volts was applied to the cell to form axis-symmetrical alignment. An axis-symmetrical alignment region was formed in each pixel region defined by the convex portions 132, and a central axis was formed at a central portion of each pixel region. Then, the cell was irradiated with UV-rays (intensity at 365 nm: 6 mW/cm$^2$) for 10 minutes at room temperature (25° C.) under the application of a voltage about 0.5 volts higher than a threshold voltage of about 2.0 volts, whereby the photocurable resin in the mixture was cured. As a result, an axis-symmetrical alignment fixing layer 142a was formed so as to cover the homeotropic alignment layer 134b. The axis-symmetrical alignment layer corresponding to the axis-symmetrical alignment layer 90b (not shown in FIG. 21) was also formed on the plasma substrate. In the present example, although a photocurable resin was used, a thermosetting resin can also be used.

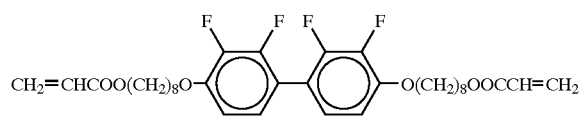

(I)

The axis-symmetrical alignment of the cell in Example 12 did not return to a homeotropic alignment state of the liquid crystal molecules even when a voltage applied to the liquid crystal layer became less than ½ $V_{th}$. It is considered that the pretilt state in axis-symmetrical alignment was kept by the axis-symmetrical alignment fixing layer 142a. Thus, after the formation of the axis-symmetrical alignment fixing layer 142a, a phenomenon that a plurality of central axes are present in the pixel regions did not occur even when a voltage of ½ $V_{th}$ or more was applied after the applied voltage was removed from the liquid crystal layer, and the homeotropic alignment state (black state) and the axis-symmetrical alignment state (white state) were able to be electrically controlled in a reversible manner. The liquid crystal molecules contained in the liquid crystal layer of the liquid crystal display device in Example 12 were provided with a pretilt angle by the axis-symmetrical alignment fixing layer 142a when no voltage is being applied. However, the shift from the homeotropic alignment was small, so that a black level when no voltage is being applied was substantially equal to that of the liquid crystal display device in Example 11. The electro-optic characteristics and viewing angle characteristics were the same as shown in FIGS. 13 and 9. Although a photocurable resin was used in the present example, a thermosetting resin can also be used.

In the liquid crystal display device of the present invention, two polarizing plates were attached in such a manner that polarization axes were placed in a crosswise direction on the display surface. As shown in FIG. 9, axis-symmetrical wide viewing angle characteristics were obtained. Since the direction of the plasma chambers is identical with that of the polarization axes of the polarizing plates, less light leaked.

By providing a phase difference plate ($\Delta n \cdot d=300$ nm) having a negative "Frisbee-type" refractive oval body between the cell and the polarizing plate, the viewing angle characteristics in a direction at an angle of 45° from the polarization axes of the polarizing plates can be further improved. Table 4 shows the results.

TABLE 4

| | Phase difference plate is provided | Phase difference plate is not provided |
|---|---|---|
| Transmittance at a viewing angle of 60° in a direction at an angle of 45° from a polarization axis | 7% | 55% |

Comparative Example 9

A liquid crystal cell was produced in the same way as in Example 11, except that the convex portions in the shape of a lattice were not formed on the counter substrate. Horizontal alignment films were formed on the surfaces of the substrates on the liquid crystal layer side, and the horizontal alignment films were subjected to a rubbing treatment, whereby a liquid crystal cell in a TN mode was produced. A liquid crystal material was injected into the cell, and the cell was heated and gradually cooled to produce TN-PALC. Polarizing plates were attached to the cell in such a manner that polarization axes were shifted by 45° from a crosswise direction on the display surface. The viewing angle characteristics of the liquid crystal display device thus obtained were as shown in FIG. 8A. As is understood from this figure, the viewing angle was much narrower, compared with those in Examples 11 and 12. Furthermore, light leakage from the attachment surface was observed in the shape of lines. Thus, a contrast was decreased.

Example 13

Figure 22A:
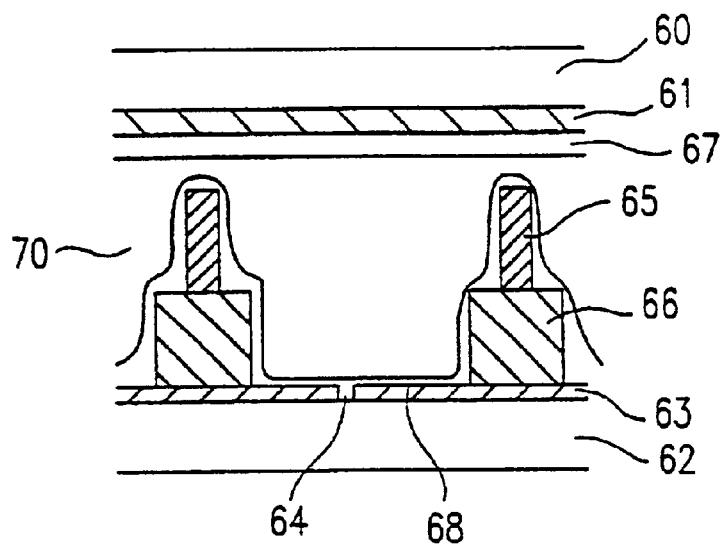
FIG. 22A is a schematic partial cross-sectional view of a liquid crystal display device in Example 13 of the present invention.
Figure 22B:
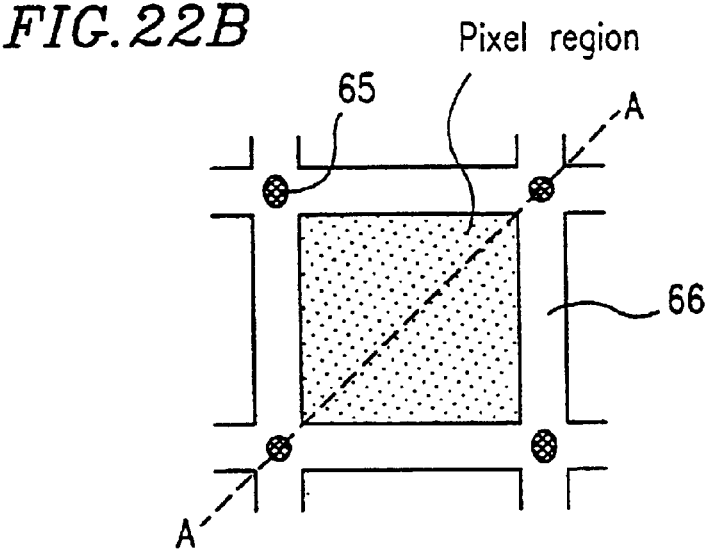
FIG. 22B is a plan view of one pixel therein.

FIG. 22A is a schematic cross-sectional view of one pixel of a liquid crystal display device in Example 13. FIG. 22B is a plan view thereof. FIG. 22A is a cross-sectional view taken along the A—A line in FIG. 22B. The structure of the liquid crystal display device will be described together with the production process.

Transparent electrodes 61 (thickness: about 100 nm) made of ITO were formed on a glass substrate 60, and JALS-204 (produced by Japan Synthetic Rubber Co., Ltd.) was spin-coated onto the transparent electrodes 61, whereby a homeotropic alignment layer 67 was formed.

Transparent electrodes 63 (thickness: about 100 nm) made of ITO were formed on a glass substrate 62. The central portion of each pixel region in the transparent electrodes 63 was removed by photolithography and etching to form an axis-symmetrical alignment central axis forming portion 64. Furthermore, convex portions 66 with a height of about 3 $\mu$m were formed with an acrylic negative resist on regions other than the pixel regions on the transparent electrode 63. Thereafter, spacers 65 with a height of about 2 $\mu$m were formed using photosensitive polyimide. The size of each pixel region defined by the spacers 65 and the convex portions 66 was prescribed to be 190 μm×325 μm. JAS-204 (produced by Japan Synthetic Rubber Co., Ltd.) was spin-coated onto the resultant substrate to form a homeotropic alignment layer 68.

Both the substrates 60 and 62 were attached to each other, and an n-type liquid crystal material (Δε=−4.0, Δn=0.08, a twist angle peculiar to the liquid crystal material=90° in a cell gap of 5 μm) to form a liquid crystal layer 70, whereby a liquid crystal cell was completed.

As the convex portions 66 and the spacers 65, photosensitive acrylate type, methacrylate type, polyimide type, and rubber type materials may be used. As long as the convex portions 66 and the spacers 65 are provided with strength against the pressure of about 400 g/Φ, any photosensitive material may be used.

In order to perform an axis-symmetrical alignment central axis forming process, the cell thus produced was supplied with an axis-symmetrical alignment central axis forming voltage of about 7 volts. After the application of a voltage, a plurality of central axes were formed in an initial state. When an axis-symmetrical alignment central axis forming voltage was continued to be applied, one central axis was formed in each pixel region, whereby one axis-symmetrical region (monodomain) was formed.

Figure 23:
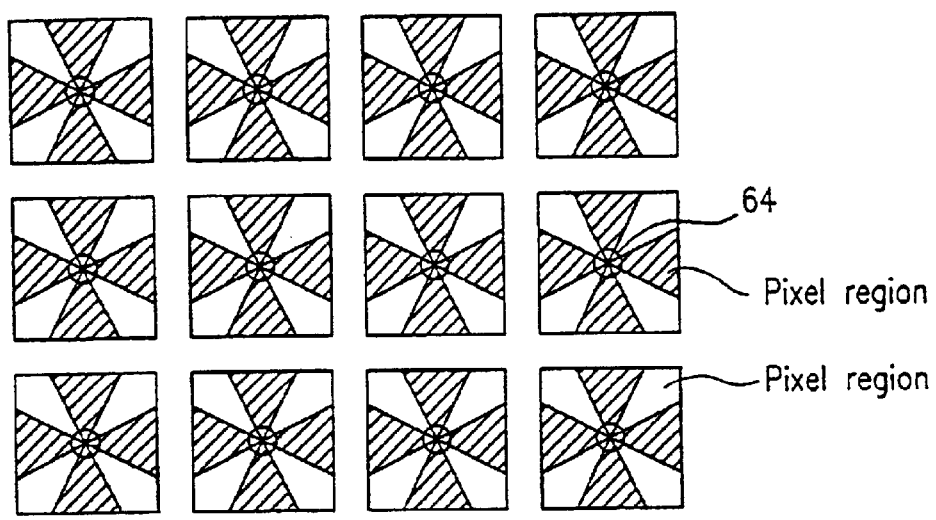
FIG. 23 is a schematic view showing results obtained by observing pixels of a liquid crystal cell produced in Example 13 of the present invention with a polarizing microscope in crossed-Nicols.

Each pixel was observed in a transmission mode using a polarizing microscope in crossed Nicols under the application of a driving voltage to the cell. Some time after the commencement of application of the voltage, it was observed that a plurality of central axes formed in an initial state immediately after the application of a voltage became one. At this time, in about 10% of the pixel regions of the liquid crystal cell, the central axes were formed shifted from the central portions of the pixel regions. By continuing to apply an axis-symmetrical alignment central axis forming voltage, the liquid crystal molecules were axis-symmetrically aligned around the central axis in each pixel region during a white display as shown in FIG. 23, and the central axes were observed to be formed at positions corresponding to the axis-symmetrical alignment central axis forming portions 64 in substantially central portions of the pixel regions.

Polarizing plates 161 were disposed in crossed-Nicols on both sides of the cell, whereby a liquid crystal display device was produced.

Figure 24:
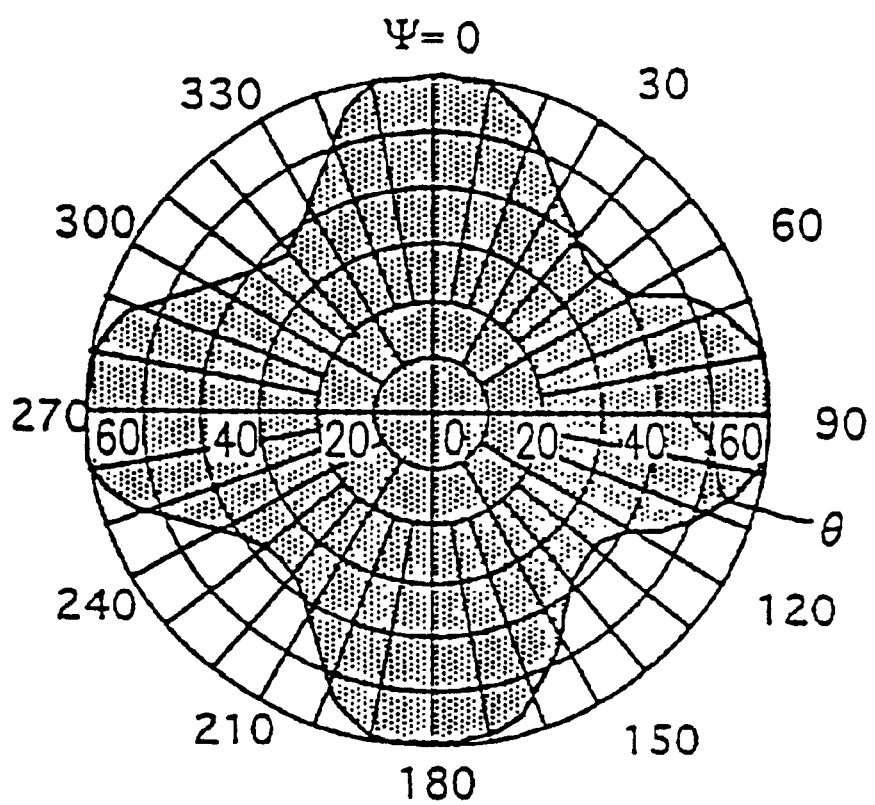
FIG. 24 is a radar chart showing viewing angle characteristics of the liquid crystal display device in Example 13 of the present invention.

FIG. 13 shows electro-optic characteristics of the liquid crystal display device in Example 13. FIG. 24 shows viewing angle characteristics of a contrast. FIG. 13 corresponds to FIG. 2. In FIG. 24, ψ represents an azimuth angle (i.e., intra-display surface angle), θ represents a viewing angle (i.e., a tilt angle from a normal to the display surface), and the hatched portion represents a region with a contrast of 10:1 or more.

Example 14

Figure 25A:
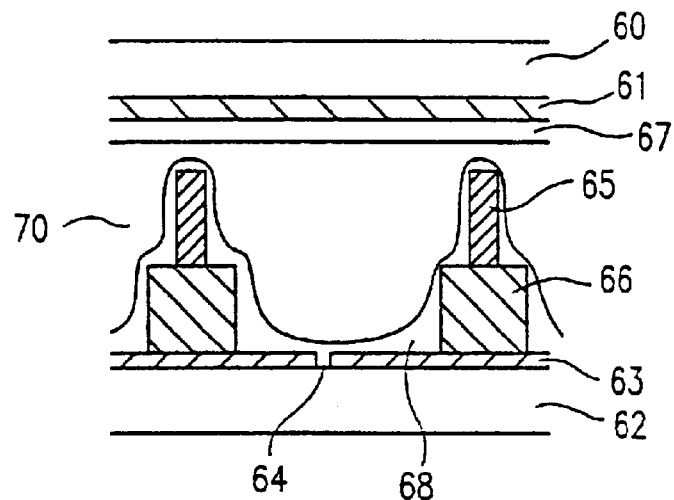
FIG. 25A is a schematic partial cross-sectional view of a liquid crystal display device in Example 14 of the present invention.
Figure 25B:
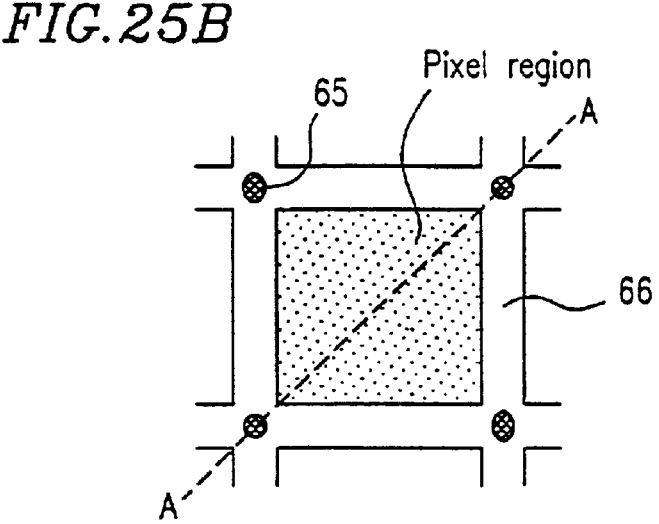
FIG. 25B is a plan view of one pixel therein.

FIG. 25A is a schematic cross-sectional view of a liquid crystal display device in Example 14. FIG. 25B is a plan view thereof. FIG. 25A is a cross-sectional view taken along the A—A line in FIG. 25B.

In Example 14, a homeotropic alignment layer 68 provided above a substrate 62 was formed so as to have a cross-section in a pixel region satisfying the relationship as shown in FIGS. 4A and 4B. That is, the homeotropic alignment layer 68 was formed in such a manner that a differential coefficient of a curve representing the changes in thickness of the homeotropic alignment layer 68 with respect to the position (from a central portion of a pixel to a peripheral portion thereof) became positive, and a differential coefficient of a curve representing the changes in thickness of a liquid crystal layer in the pixel region became negative. More specifically, the cross-section of the homeotropic alignment layer 68 in the pixel region had the shape of a mortar, and an axis-symmetrical alignment central axis forming portion 64 was provided in a pixel electrode 63 at the deepest position of the cross-section of the homeotropic alignment layer 68. A liquid crystal cell was produced in the same way as in Example 13.

In order to perform an axis-symmetrical alignment central axis forming process, the cell thus produced was supplied with an axis-symmetrical alignment central axis forming voltage of about 7 volts. After the application of a voltage, a plurality of central axes were formed in an initial state. When an axis-symmetrical alignment central axis forming voltage was continued to be applied, one central axis was formed in each pixel region, whereby one axis-symmetrical region (monodomain) was formed.

Each pixel was observed in a transmission mode using a polarizing microscope in crossed Nicols under the application of a driving voltage to the cell. Some time after the commencement of application of the voltage, it was observed that a plurality of central axes formed in an initial state immediately after the application of a voltage became one. Each central axis thus formed was provided in a substantially central portion of the pixel region corresponding to the deepest portion of the mortar-shaped cross-section. By continuing to apply an axis-symmetrical alignment central axis forming voltage, the liquid crystal molecules were axis-symmetrically aligned around the central axis in each pixel region during a white display as shown in FIG. 23, and the central axes were observed to be formed at positions corresponding to the axis-symmetrical alignment central axis forming portions 64 in substantially central portions of the pixel regions.

Polarizing plates were disposed in crossed Nicols on both sides of the cell, whereby a liquid crystal display device was produced.

The liquid crystal display device in Example 14 had almost the same electro-optic characteristics and viewing angle characteristics of a contrast as those in Example 13.

Example 15

Liquid crystal cells were produced in the same way as in Example 13, except that the size of each pixel was prescribed to be 100 μm×100 μm, and the area of the axis-symmetrical alignment central axis forming portion 64 at a central portion of the pixel region was prescribed to be 0 μm$^2$, 25 μm$^2$, 100 μm$^2$, 400 μm$^2$, and 900 μm$^2$. Polarizing plates were placed in crossed-Nicols on both sides of each cell, whereby liquid crystal display devices were completed.

In the present example, each pixel was observed in a transmission mode with a polarizing microscope in crossed-Nicols under the application of a driving voltage to the cells. The following Table 5 shows the results obtained by evaluating roughness of a display with each cell tilted under the application of a voltage which provides gray scales. In Table 5, ○ represents a display of good quality having almost no roughness; Δ represents a display with negligible roughness; X represents a display with roughness; Sb represents an area of an axis-symmetrical alignment central axis forming portion; and A represents an area of a pixel region.

TABLE 5

| Sb ($\mu m^2$) | A ($\mu m^2$) | Sb/A (%) | Evaluation |
|---|---|---|---|
| 0 | 10000 | 0 | X |
| 25 | 10000 | 0.25 | ○ |
| 100 | 10000 | 1.0 | ○ |
| 400 | 10000 | 4.0 | Δ |
| 900 | 10000 | 9.0 | X |

As is understood from Table 5, it is preferable that the axis-symmetrical alignment central axis forming portion is provided so that Sb satisfies 0<Sb/A<4%.

Example 16

A method for stabilizing the axis-symmetrical alignment state of liquid crystal molecules by forming an axis-symmetrical alignment fixing layer on a surface of either one of substrates on a liquid crystal layer side will be described, the method including an axis-symmetrical alignment central axis forming process in the course of the production of a liquid crystal display device.

Figure 26:
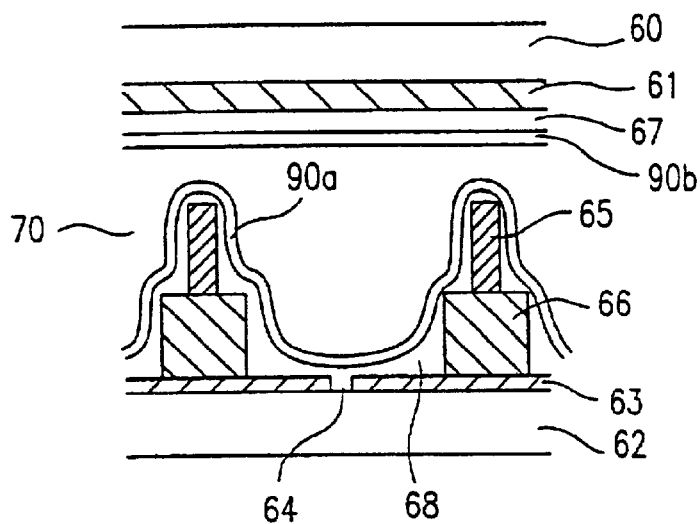
FIG. 26 is a schematic partial cross-sectional view of a liquid crystal display device in Example 16 of the present invention.

FIG. 26 is a schematic cross-sectional view of a liquid crystal display device in Example 16. The liquid crystal display device in Example 16 has the same structure as that in Example 13, except that axis-symmetrical alignment fixing layers 90a and 90b are provided on homeotropic alignment layers 68 and 67, respectively.

Substrates having cross-sectional structures shown in FIG. 26 were produced in the same way as in Example 13. Transparent electrodes 61 (thickness: about 100 nm) made of ITO were formed on a glass substrate 60. JALS-204 (produced by Japan Synthetic Rubber Co., Ltd.) was spin-coated to form a homeotropic alignment layer 67.

Transparent electrodes 63 (thickness: about 100 nm) made of ITO were formed on a glass substrate 62, and a central portion of a pixel region was removed by photolithography and etching, whereby an axis-symmetrical alignment central axis forming portion 64 was formed. Furthermore, convex portions 66 with a height of about 3 $\mu$m were formed with an acrylic negative resist outside of the pixel region on the transparent electrode 63. Thereafter, spacers 65 with a height of about 2 $\mu$m were formed with photosensitive polyimide. The size of the pixel region defined by the spacers 65 and the convex portions 66 was prescribed to be 100 $\mu$m×100×m. JALS-204 (produced by Japan Synthetic Rubber Co., Ltd.) was spin-coated onto the resultant substrate, whereby a homeotropic alignment layer 68 was formed.

The two substrates were attached to each other to complete a liquid crystal cell. The structure of the cell thus obtained was the same as that of the liquid crystal display device in Example 13.

In the present example, the following precursor mixture was injected into the cell thus produced. The precursor mixture contains an n-type liquid crystal material (Δε=−4.0; Δn=0.08; a chiral angle=90° in a cell gap of 5 $\mu$m), and 0.3 wt % of compound A (photocurable resin) represented by the following Formula I, and 0.1 wt % of Irgacure 651. After the injection, an axis-symmetrical alignment central axis forming process was performed by applying an axis-symmetrical alignment central axis forming voltage of about 5 volts to the cell. Furthermore, the cell was irradiated with UV-rays (intensity at 365 nm: 6 mW/cm²) at room temperature (25° C.) for 10 minutes under the application of the axis-symmetrical alignment central axis forming voltage, whereby the photocurable material in the precursor mixture was cured. As a result, the axis-symmetrical alignment fixing layers 90a and 90b were formed so as to cover the homeotropic alignment layers 68 and 67 on the substrates in the course of the axis-symmetrical alignment central axis forming process. The axis-symmetrical alignment fixing layers 90a and 90b contain a polymer of a cured photocurable or thermosetting material, such as an acrylate type material, a methacrylate type material, a styrene type material, and derivatives thereof, contained in the precursor mixture.

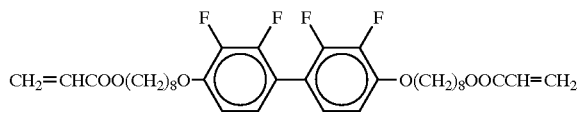

(I)

Polarizing plates were attached to both sides of the cell to complete a liquid crystal display device.

Each pixel was observed in a transmission mode with a polarizing microscope in crossed-Nicols under the application of a voltage to the cell in Example 16. Even immediately after the application of a voltage, a single central axis was formed in each pixel region without a plurality of central axes being formed. Thereafter, the voltage applied to the cell was once removed, and a voltage of ½ $V_{th}$ or more was applied to the cell again. However, a phenomenon that a plurality of central axes are present in each pixel region did not occur, and a single central axis was formed. The reason for this is considered to be as follows: even when a voltage applied to the liquid crystal layer decreased to less than ½ $V_{th}$, the liquid crystal molecules did not return to a homeotropic alignment state; a pretilt state in axis-symmetrical alignment was kept by the axis-symmetrical alignment fixing layer 90a. Thus, in the present example, a black display is able to be performed when no voltage is being applied. Furthermore, it is not required to perform an axis-symmetrical alignment central axis forming process before a display operation. Although the liquid crystal molecules were provided with a pretilt angle by the axis-symmetrical alignment fixing layer 90a, the shift from homeotropic alignment was small. A black level when no voltage is being applied was substantially the same as that of the liquid crystal display device in Example 13. The electro-optic characteristics and viewing angle characteristics were the same as those shown in FIGS. 13 and 24. In the present example, although a photocurable resin was used, a thermosetting resin may be used.

Example 17

Liquid crystal display devices were produced in the same way as in Example 15 by injecting the precursor mixture with the varying content of the compound A into the cell in Example 16.

The content of the compound A was varied from 0.05 wt % to 6 wt %. The light transmittance of the liquid crystal display devices when no voltage is being applied were measured, and the devices were observed to see if a stable axis-symmetrical alignment state was formed.

As a result, when the content of the photocurable material was less than about 0.1 wt %, the axis-symmetrical alignment fixing process was not able to be performed effectively. When the content of the photocurable material was more than about 6 wt %, the homeotropic alignment of the liquid crystal molecules was disturbed to increase light leakage when no voltage is being applied. Thus, the content of the photocurable material is preferably in the range of about 0.1 wt % to 6 wt %.

Example 18

In the present example, the following phase difference plates were placed between a pair of polarizing plates and a liquid crystal cell of the liquid crystal display device in Example 13 in such a manner that a delay axis of each phase difference plate was orthogonal to an absorption axis of each polarizing plate.

The phase difference plate has optically negative birefringence, and satisfies $n_x=n_y$, $n_x>n_z$, $n_y>n_z$, where $n_x$, $n_y$ are primary refractive indexes in an in-plane direction of a refractive oval body, and $n_z$ is a primary refractive index in a thickness direction thereof.

Supposing that the thickness of the phase difference plate is $d_f$, the retardation in the thickness direction was $(n_x-n_z)d_f=160$ nm.

Figure 27:
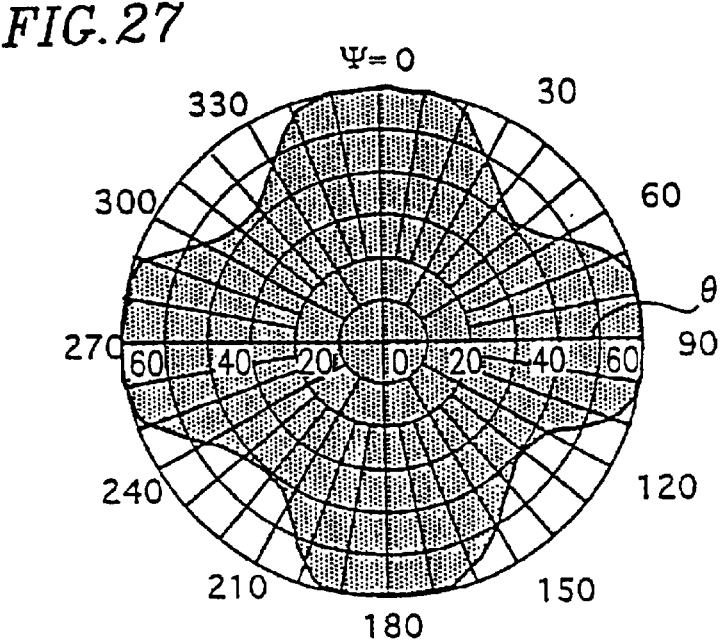
FIG. 27 is a radar chart showing viewing angle characteristics of a liquid crystal display device in Example 18 of the present invention.

FIG. 27 shows the results obtained by measuring viewing angle characteristics of the liquid crystal display device in Example 18. In FIG. 27, ψ represents an azimuth angle (i.e., intra-display surface angle), θ represents a viewing angle (i.e., a tilt angle from a normal to the display surface), and the hatched portion represents a region with a contrast of 10:1 or more.

As is apparent from FIG. 27, the viewing angle of the liquid crystal display device in the present example was larger than that of the liquid crystal display device in Example 13 shown in FIG. 24, and the display quality was uniform.

Example 19

In the present example, the following phase difference films were placed between a pair of polarizing plates and a liquid crystal cell of the liquid crystal display device in Example 13 in such a manner that a delay axis of each phase difference film was orthogonal to an absorption axis of each polarizing plate.

The phase difference film has optically negative birefringence, and satisfies $n_x>n_y>n_z$, where $n_x$, $n_y$ are primary refractive indexes in an in-plane direction of a refractive oval body, and $n_z$ is a primary refractive index in a thickness direction thereof.

Supposing that the thickness of the phase difference film is $d_f$, the retardation in the thickness direction was $(n_z-n_y)d_f=170$ nm. The retardation in an in-plane direction was $(n_x-n_y)d_f=42$ nm.

Figure 28:
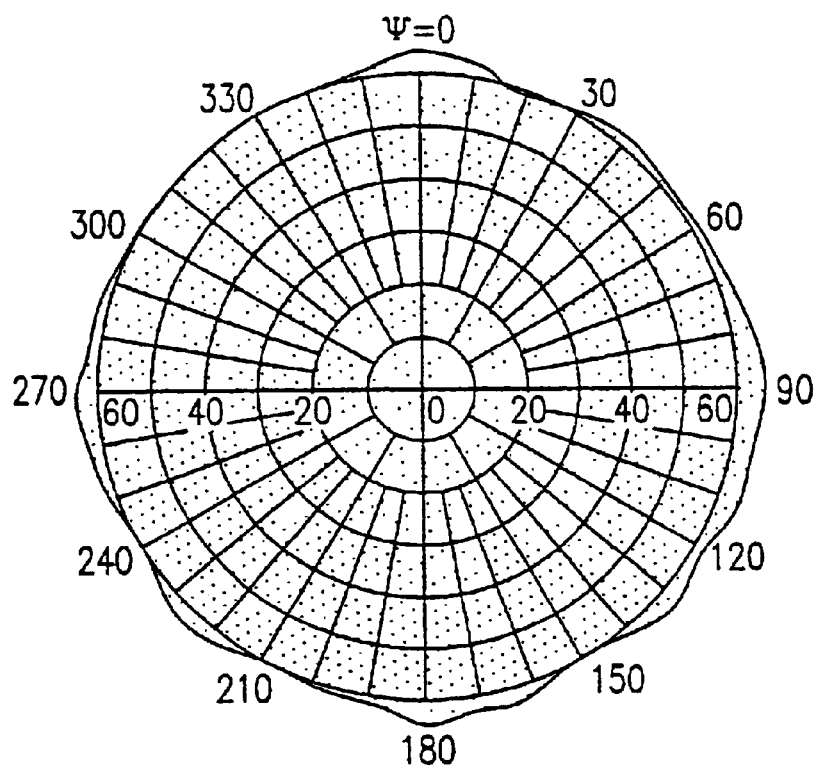
FIG. 28 is a radar chart showing viewing angle characteristics of a liquid crystal display device in Example 19 of the present invention.

FIG. 28 shows the results obtained by measuring viewing angle characteristics of the liquid crystal display device in Example 19. In FIG. 28, t represents an azimuth angle (i.e., intra-display surface angle), θ represents a viewing angle (i.e., a tilt angle from a normal to the display surface), and the hatched portion represents a region with a contrast of 10:1 or more.

As is apparent from FIG. 28, the viewing angle of the liquid crystal display device in the present example was larger than that of the liquid crystal display device in Example 13 shown in FIG. 24, and display quality was uniform.

Comparative Example 10

Figure 29:
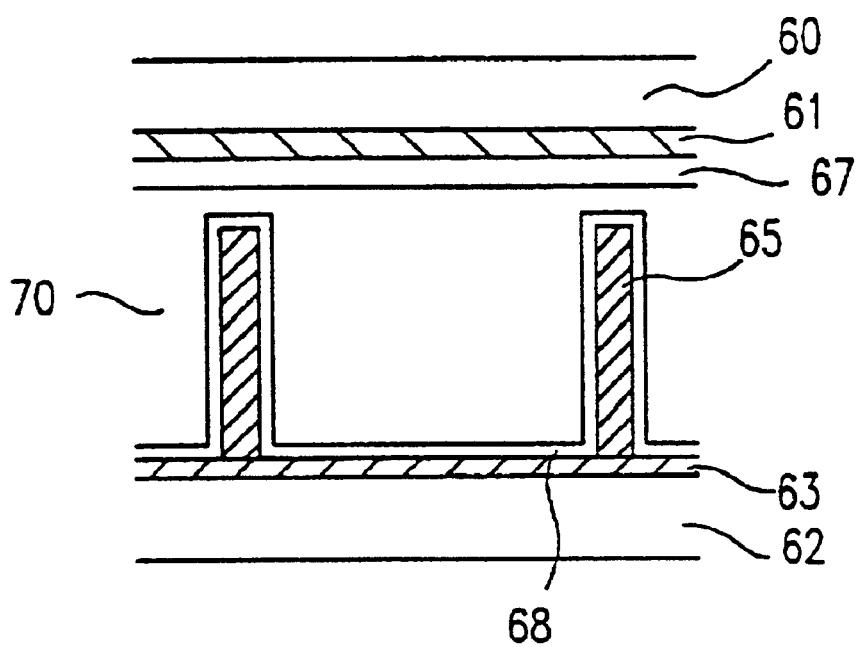
FIG. 29 is a schematic partial cross-sectional view of a liquid crystal display device in Comparative Example 10.
Figure 30A:
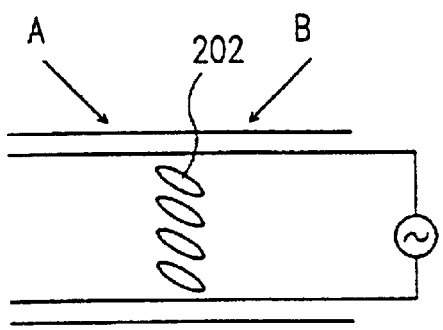
FIGS. 30A and 30B are schematic views illustrating viewing angle dependence of a conventional liquid crystal display device.
Figure 30B:
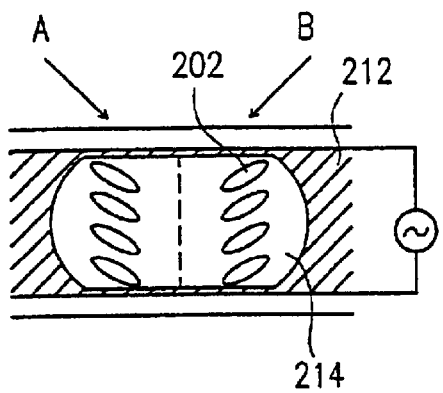
Figure 31:
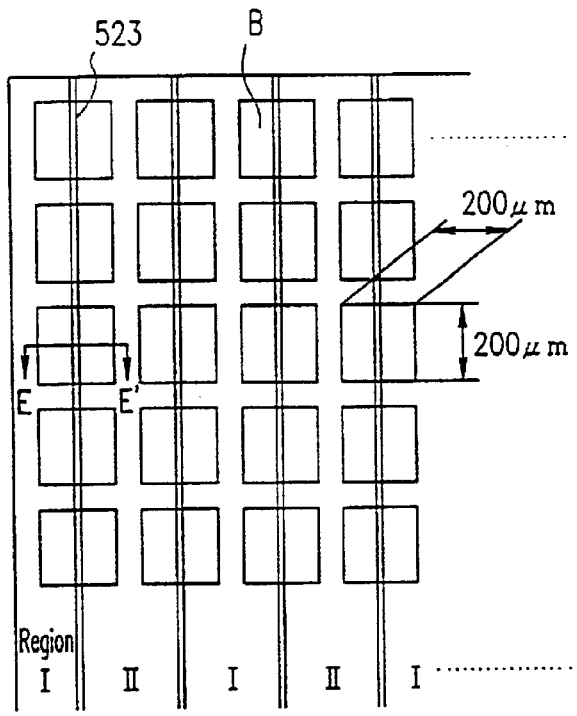
FIG. 31 is a schematic plan view of a conventional liquid crystal display device in a wide viewing angle mode.
Figure 32:
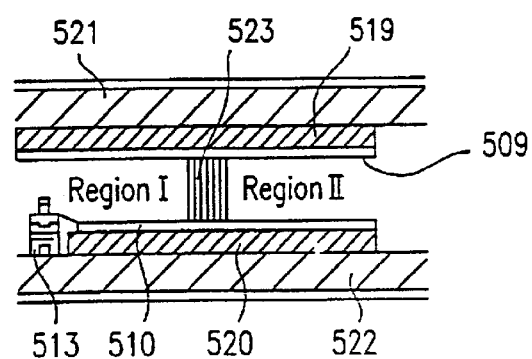
FIG. 32 is a cross-sectional view taken along the E–E' line in FIG. 31.
Figure 33:
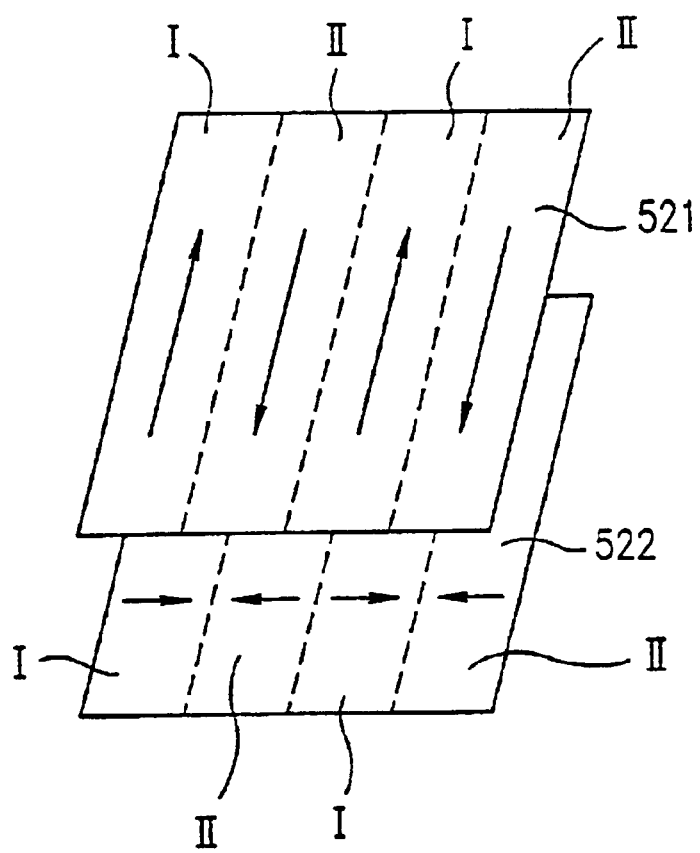
FIG. 33 is a schematic view illustrating a method for producing the conventional liquid crystal display device shown in FIG. 31.
Figure 34:
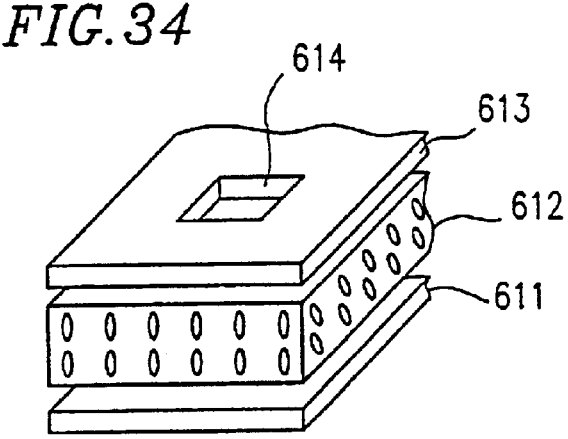
FIG. 34 is a schematic view illustrating the operation principle of a conventional liquid crystal display device in a wide viewing angle mode.
Figure 35:
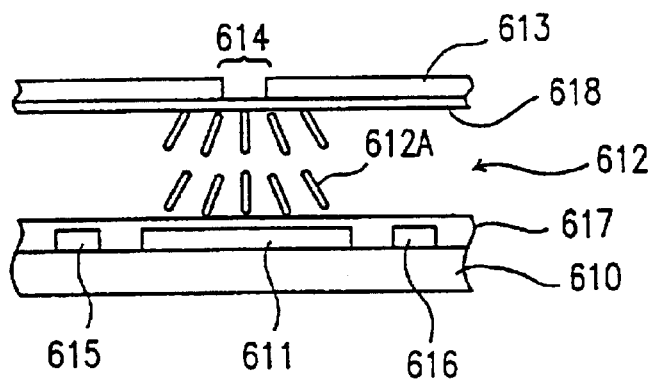
FIG. 35 is a schematic cross-sectional view of the conventional liquid crystal display device in a wide viewing angle mode.
Figure 36:
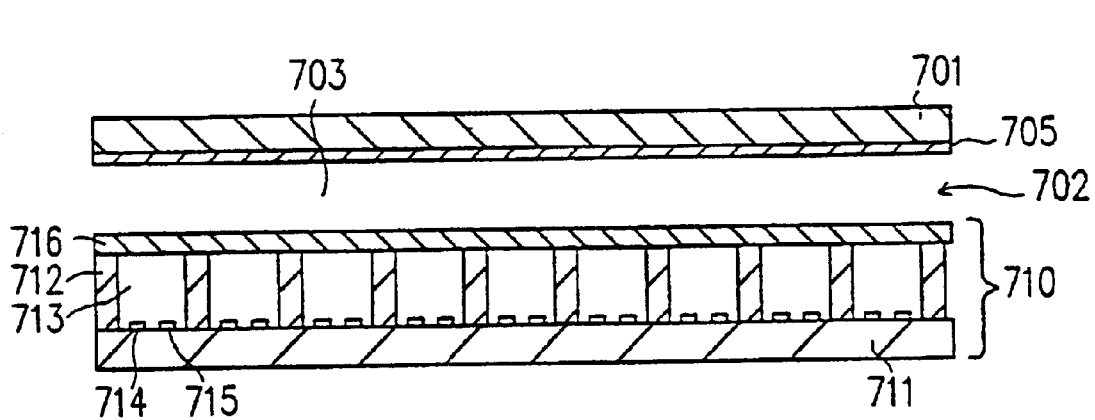
FIG. 36 is a schematic cross-sectional view of a conventional PALC.
Figure 37:
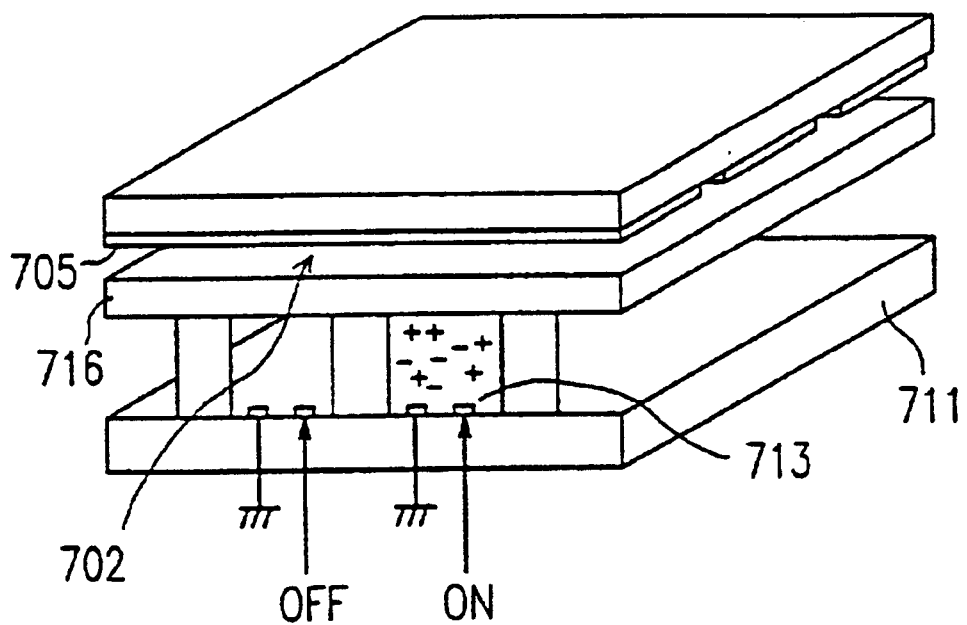
FIG. 37 is a schematic view illustrating the operation principle of the conventional PALC.
Figure 38:
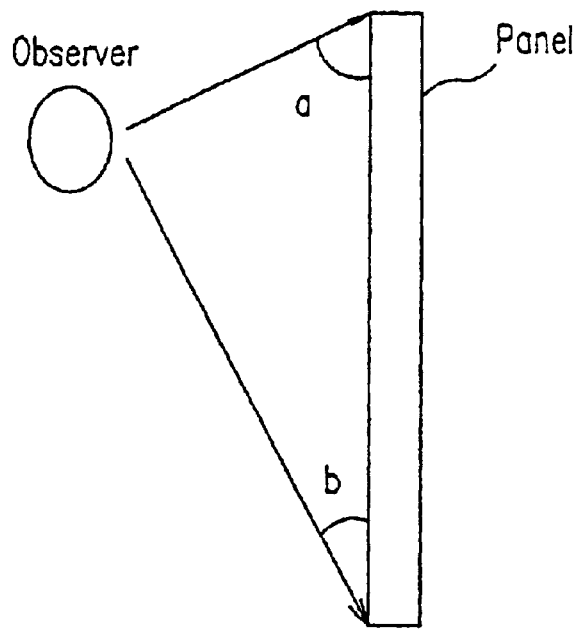
FIG. 38 is a schematic view illustrating the difference in viewing angle in a large display device.

In Comparative Example 10, as shown in FIG. 29, the homeotropic alignment layer 68 was directly formed on the transparent electrode 63 provided on the surface of the substrate 62, and the spacers 65 were formed with photo-sensitive polyimide in the same way as in Example 13. More specifically, in Comparative Example 10, the convex portions 66 were not formed. The axis-symmetrical alignment central axis forming portion 64 was not formed, either.

The substrate on a lower side thus obtained was attached to a counter substrate on an upper side formed in the same way as in Example 13 to produce a liquid crystal cell. The same material as that in Example 13 was injected into the cell, and polarizing plates were placed in crossed-Nicols on both sides of the cell.

In the liquid crystal display device in Comparative Example 10, the liquid crystal molecules were randomly aligned, and disclination lines were randomly formed. The liquid crystal display device was observed under the application of a voltage, a display with roughness was observed in gray scales.

Comparative Example 11

In Comparative Example 11, the homeotropic alignment layer 68 was directly formed on the transparent electrode 63 provided on the surface of the substrate 62 shown in FIG. 22A. Thereafter, the spacers 65 were formed with photo-sensitive polyimide in the same way as in Example 13. More specifically, in Comparative Example 11, the convex portions 66 as shown in FIG. 22A were not formed, and the axis-symmetrical alignment central axis forming portion 64 was formed on the pixel electrode 63.

The substrate on a lower side thus obtained was attached to a counter substrate on an upper side formed in the same way as in Example 13 to produce a liquid crystal cell. The same material as that in Example 13 was injected into the cell, and polarizing plates were placed in crossed-Nicols on both sides of the cell.

In the liquid crystal display device in Comparative Example 11, the liquid crystal molecules were randomly aligned, and disclination lines were randomly formed in the same way as in Comparative Example 10. The liquid crystal cell was observed under the application of an axis-symmetrical alignment central axis forming voltage, a display with roughness was observed in gray scales.

As described above, according to the present invention, a liquid crystal display device (including a plasma address LCD) with outstanding viewing angle characteristics and a high contrast, and a method for producing the same are provided. The device includes a liquid crystal region where liquid crystal molecules are vertically aligned when no voltage is being applied and are axis-symmetrically aligned under the application of a voltage.

The liquid crystal display device of the present invention has outstanding viewing angle characteristics because of a liquid crystal region which is switched between homeotropic alignment and axis-symmetrical alignment. Furthermore, the device uses a liquid crystal material with a negative dielectric anisotropy, performing a display in a normally black mode in which a homeotropic alignment state is obtained when no voltage is being applied. Therefore, a display with a high contrast can be provided. In particular, by controlling the positions of the axis-symmetrical alignment central axes of the liquid crystal molecules under the application of a voltage, roughness of a display in gray scales is eliminated, whereby display quality can be remarkably improved.

More specifically, since the convex portions defining the pixel regions are formed on the surface of at least one of the substrates on the liquid crystal layer side, each pixel region exhibiting axis-symmetrical alignment is defined by the convex portions. Furthermore, a treatment for controlling the positions of the axis-symmetrical alignment central axes is performed, so that the position of the axis-symmetrical alignment central axis in each pixel region exhibiting axis-symmetrical alignment is defined.

Examples of the treatment for controlling the positions of the axis-symmetrical alignment central axes include: (i) performing an axis-symmetrical alignment central axis forming process in which a desired voltage is applied for a desired period of time or longer; (ii) prescribing Sa so as to satisfy 0<Sa/A<4%, where Sa represents an area of a region in which the liquid crystal molecules keep a homeotropic alignment state under the application of an axis-symmetrical alignment central axis forming voltage and A represents an area of a pixel region; (iii) forming an axis-symmetrical alignment central axis forming portion at a substantially central position or at a predetermined position in each of a plurality of pixel regions; (iv) prescribing the thickness of the liquid crystal layer in the pixel region so as to become largest at a central portion of the pixel region and continuously decrease from the central portion to a peripheral portion of the pixel region; and (v) forming an axis-symmetrical alignment fixing layer on the surface of at least one of the substrates on the liquid crystal layer side.

The liquid crystal display device of the present invention is preferably used, for example, for a portable information terminal used by a number of people, a personal computer, a word processor, amusement equipment, education equipment, a flat display used in a TV apparatus, and a display plate, window, door and wall utilizing a shutter effect. The liquid crystal display device of the present invention is also preferably used as a large display apparatus such as a high definition TV (HDTV) and a display for a CAD.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A liquid crystal display device comprising a pair of substrates and a continuous liquid crystal layer provided between the substrates, wherein liquid crystal molecules in the liquid crystal layer have a negative dielectric anisotropy, and the liquid crystal molecules are aligned in a direction substantially vertical to the substrates when no voltage is being applied and axis-symmetrically aligned in each of a plurality of pixel regions under application of a voltage, wherein a thickness ($d_{in}$) of the liquid crystal layer in the pixel regions is larger than a thickness ($d_{out}$) of the liquid crystal layer outside of the pixel regions, and the device includes a homeotropic alignment layer in a region corresponding to the pixel regions on a surface of at least one of the substrates on the liquid crystal layer side.

2. A liquid crystal display device according to claim 1, wherein at least one of the substrates has convex portions defining the pixel regions on a surface on the liquid crystal layer side.

3. A liquid crystal display device according to claim 1, wherein the thickness of the liquid crystal layer in the pixel regions is largest at a central portion of the pixel regions and continuously decreases toward a peripheral portion of each of the pixel regions.

4. A liquid crystal display device according to claim 3, wherein the thickness of the liquid crystal layer in the pixel regions is axis-symmetrically changed around the central portion of the pixel region.

5. A liquid crystal display device according to claim 1, further comprising a projection at the central portion of the pixel regions, wherein the liquid crystal molecules are axis-symmetrically aligned around the projection under the application of a voltage.

6. A liquid crystal display device according to claim 1, wherein a retardation d·Δn of the liquid crystal layer is in a range of about 300 nm to about 500 n m.

7. A liquid crystal display device according to claim 1, wherein a twist angle of the liquid crystal layer is in a range of about 45° to about 110°.

8. A liquid crystal display device according to claim 1, comprising a pair of polarizing plates disposed in crossed Nicols on both sides of the liquid crystal layer, a phase difference plate having a relationship, in which a refractive index $n_{x,y}$ in an in-plane direction is greater than a refractive index $n_z$ in a direction vertical to a plane, being provided on at least one of the polarizing plates.

9. A liquid crystal display device according to claim 1, wherein an axis-symmetrical alignment fixing layer which provides the liquid crystal molecules with an axis-symmetrical pretilt angle is further formed on a surface of at least one of the substrates on the liquid crystal layer side.

10. A liquid crystal display device according to claim 9, wherein the axis-symmetrical alignment fixing layer contains a photocurable resin.

11. A liquid crystal display device, comprising;
a pair of substrates and a continuous liquid crystal layer provided between the substrates, wherein an array of pixel regions is between the pair of substrates,
wherein liquid crystal molecules in the liquid crystal layer have a negative dielectric anisotropy, and the liquid crystal molecules are aligned in a direction substantially vertical to the substrates when no driving voltage is being applied and axis-symmetrically aligned around an axis-symmetrical alignment central axis in each of a plurality of pixel regions under application of a driving voltage,
wherein a thickness ($d_{in}$) of the liquid crystal layer in the pixel regions is larger than a thickness ($d_{out}$) of the liuqid crystal layer outside of the pixel regions, and
a convex portion defining each of the pixel regions is provided on a surface of at least one of the substrates on the liquid crystal layer side, and said convex portion includes a treatment for controlling a position of the axis-symmetrical alignment central axis.

12. A liquid crystal display device according to claim 11, comprising a region in which the liquid crystal molecules keep a homeotropic alignment state under application of an axis-symmetrical alignment central axis forming voltage at each predetermined position in the plurality of pixel regions.

13. A liquid crystal display device according to claim 11, wherein a thickness of the liquid crystal layer in the pixel region is thickest at a center of each of the pixel regions and thinnest an an outer periphery of the pixel regions.

14. A liquid crystal display device according to claim 13, wherein the thickness of the liquid crystal layer in each of the pixel regions is largest at a central portion of each of the pixel regions and continuously decreases from the central portion to a peripheral portion of the pixel regions.

15. A liquid crystal display device according to claim 14, wherein the thickness of the liquid crystal layer in the pixel regions is axis-symmetrically changed around the central portion of the pixel regions.

16. A liquid crystal display device according to claim 11, wherein an axis-symmetrical alignment fixing layer is provided on a surface of at least one of the substrates on the liquid crystal layer side.

17. A liquid crystal display device according to claim 16, wherein the axis-symmetrical alignment fixing layer contains a photocurable resin.

18. A liquid crystal display device comprising:

a pair of substrates and a liquid crystal layer provided between the substrates, wherein liquid crystal molecules in the liquid crystal layer have a negative dielectric anisotropy, and the liquid crystal molecules are aligned in a direction substantially vertical to the substrates when no driving voltage is being applied and axis-symmetrically aligned around an axis-symmetrical alignment central axis in each of a plurality of pixel regions under application of a driving voltage, and a convex portion defining each of the pixel regions is provided on a surface of at least one of the substrates on the liquid crystal layer side, and said convex portion includes a treatment for controlling a position of the axis-symmetrical alignment central axis, and each pixel region includes an Sa region in which the liquid crystal molecules keep a homeotropic alignment state under application of an axis-symmetrical alignment central axis forming voltage, wherein the Sa region is an area of the pixel region in which the liquid crystal molecules keep a homeotropic alignment state under the application of the axis-symmetrical alignment central axis forming voltage, A is an area of the pixel region, and Sa/A satisfies the relationship 0<Sa/A<4%.

19. A liquid crystal display device according to claim 18, wherein Sb is an area of the axis-symmetrical alignment central axis forming portion, A is an area of the pixel region, and Sb/A satisfies the relationship 0<Sb/A<4%.

20. A liquid crystal display device comprising:

a pair of substrates and a liquid crystal layer provided between the substrates, wherein liquid crystal molecules in the liquid crystal layer have a negative dielectric anisotropy, and the liquid crystal molecules are aligned in a direction substantially vertical to the substrates when no driving voltage is being applied and axis-symmetrically aligned around an axis-symmetrical alignment central axis in each of a plurality of pixel regions under application of a driving voltage, convex portions defining the pixel region are provided on a surface of at least one of the substrates on the liquid crystal layer side, and a treatment for controlling a position of the axis-symmetrical alignment central axis is conducted, each pixel region includes an Sb region in which the liquid crystal molecules keep a homeotropic alignment state under application of an axis-symmetrical alignment central axis forming voltage at each predetermined position, and an axis-symmetrical alignment central axis forming portion at a predetermined position in each of the plurality of pixel regions, and the axis-symmetrical alignment central axis of the liquid crystal molecules corresponds to the axis-symmetrical alignment central axis forming portion, wherein the Sb region is an area aligned with the axis-symmetrical alignment central axis forming portion, A is an area of the pixel region, and Sb/A satisfies the relationship 0<Sb/A<4%.

* * * * *